(12) United States Patent
Beden et al.

(10) Patent No.: US 10,420,875 B2
(45) Date of Patent: Sep. 24, 2019

(54) METHOD FOR QUERYING A SPECIFICATION FEATURE OF A MEDICAL TECHNICAL FUNCTIONAL MEANS, A MEDICAL TECHNICAL FUNCTIONAL MEANS, A MEDICAL DEVICE AND A CONTROL UNIT

(71) Applicant: Fresenius Medical Care Deutschland GmbH, Bad Homburg (DE)

(72) Inventors: Josef Beden, Mainz-Kastel (DE); Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 90 days.

(21) Appl. No.: 15/407,571

(22) Filed: Jan. 17, 2017

(65) Prior Publication Data

US 2017/0151383 A1 Jun. 1, 2017

Related U.S. Application Data

(63) Continuation of application No. 13/352,843, filed on Jan. 18, 2012, now Pat. No. 9,550,021.

(Continued)

(30) Foreign Application Priority Data

Jan. 18, 2011 (DE) .................. 10 2011 008 856

(51) Int. Cl.
*A61M 1/36* (2006.01)
*A61B 90/90* (2016.01)
(Continued)

(52) U.S. Cl.
CPC .......... *A61M 1/3672* (2013.01); *A61B 90/90* (2016.02); *A61B 90/96* (2016.02); *A61B 90/98* (2016.02);
(Continued)

(58) Field of Classification Search
USPC ....................................................... 235/375
See application file for complete search history.

(56) References Cited

U.S. PATENT DOCUMENTS

| 5,317,506 A | 5/1994 | Coutre et al. |
| 6,468,242 B1 | 10/2002 | Wilson et al. |
| (Continued) | | |

FOREIGN PATENT DOCUMENTS

| CN | 101669122 | 3/2010 |
| DE | 19814687 | 2/1999 |
| (Continued) | | |

OTHER PUBLICATIONS

International Search Report issued in PCT/EP2012/000160, dated Jul. 3, 2012.

(Continued)

*Primary Examiner* — Michael G Lee
*Assistant Examiner* — David Tardif
(74) *Attorney, Agent, or Firm* — Fish & Richardson P.C.

(57) ABSTRACT

The present invention relates to a method for querying a specification feature arranged in, at or on a medical technical functional means, the method comprising the step of: querying the specification feature by means of a medical device functionally coupled to or to be coupled to the medical technical functional means or by means of a device or means connected to or being arranged in signal transmission with the medical technical treatment apparatus. The invention further relates to a medical technical functional means, a medical device and a control unit. Furthermore, the present invention relates to a digital storage medium, a computer program product and a computer program.

22 Claims, 20 Drawing Sheets

Related U.S. Application Data

(60) Provisional application No. 61/433,533, filed on Jan. 18, 2011.

(51) Int. Cl.
   *G06F 16/245* (2019.01)
   *G06F 16/955* (2019.01)
   *A61B 90/96* (2016.01)
   *A61B 90/98* (2016.01)

(52) U.S. Cl.
   CPC ......... *A61M 1/3621* (2013.01); *G06F 16/245* (2019.01); *G06F 16/9554* (2019.01); *A61M 2205/12* (2013.01); *A61M 2205/18* (2013.01); *A61M 2205/3306* (2013.01); *A61M 2205/3317* (2013.01); *A61M 2205/3368* (2013.01); *A61M 2205/3584* (2013.01); *A61M 2205/3592* (2013.01); *A61M 2205/52* (2013.01); *A61M 2205/581* (2013.01); *A61M 2205/583* (2013.01); *A61M 2205/6018* (2013.01); *A61M 2205/6054* (2013.01); *A61M 2205/6072* (2013.01); *A61M 2205/6081* (2013.01)

(56) References Cited

U.S. PATENT DOCUMENTS

| | | | |
|---|---|---|---|
| 7,083,608 | B2 | 8/2006 | Tomita et al. |
| 2002/0038392 | A1 | 3/2002 | De La Huerga |
| 2002/0147423 | A1 | 10/2002 | Burbank et al. |
| 2005/0277890 | A1 | 12/2005 | Stewart et al. |
| 2008/0068197 | A1 | 3/2008 | Neubauer et al. |
| 2009/0009290 | A1 | 1/2009 | Kneip et al. |
| 2009/0012449 | A1 | 1/2009 | Lee et al. |
| 2009/0118594 | A1* | 5/2009 | Zdeblick ................. A61B 5/117 600/300 |
| 2010/0089837 | A1 | 4/2010 | Inoue et al. |
| 2010/0140149 | A1* | 6/2010 | Fulkerson ............... A61M 1/14 210/85 |
| 2010/0274172 | A1 | 10/2010 | Guenther et al. |
| 2010/0282834 | A1 | 11/2010 | Devergne et al. |
| 2011/0035690 | A1 | 2/2011 | Durrell et al. |
| 2011/0186517 | A1* | 8/2011 | Hedmann ............. A61M 1/282 210/645 |
| 2012/0095351 | A1* | 4/2012 | Klose ................. A61M 1/3639 600/483 |

FOREIGN PATENT DOCUMENTS

| | | |
|---|---|---|
| DE | 20 2005 016 276 | 12/2005 |
| DE | 10 2009 024 606 | 12/2010 |
| JP | 11-319075 | 11/1999 |
| JP | 2005-509496 | 4/2005 |
| JP | 2006-314458 | 11/2006 |
| JP | 2008-104682 | 5/2008 |
| JP | 2010-532235 | 10/2010 |
| WO | WO 03/043677 | 5/2003 |
| WO | WO 2008/152810 | 12/2008 |
| WO | WO 2009/006496 | 1/2009 |
| WO | WO 2009/081241 | 7/2009 |
| WO | WO 2009/135835 | 11/2009 |

OTHER PUBLICATIONS

International Preliminary Report on Patentability in Application No. PCT/EP2012/000160, dated Jul. 23, 2013, 7 pages.

* cited by examiner

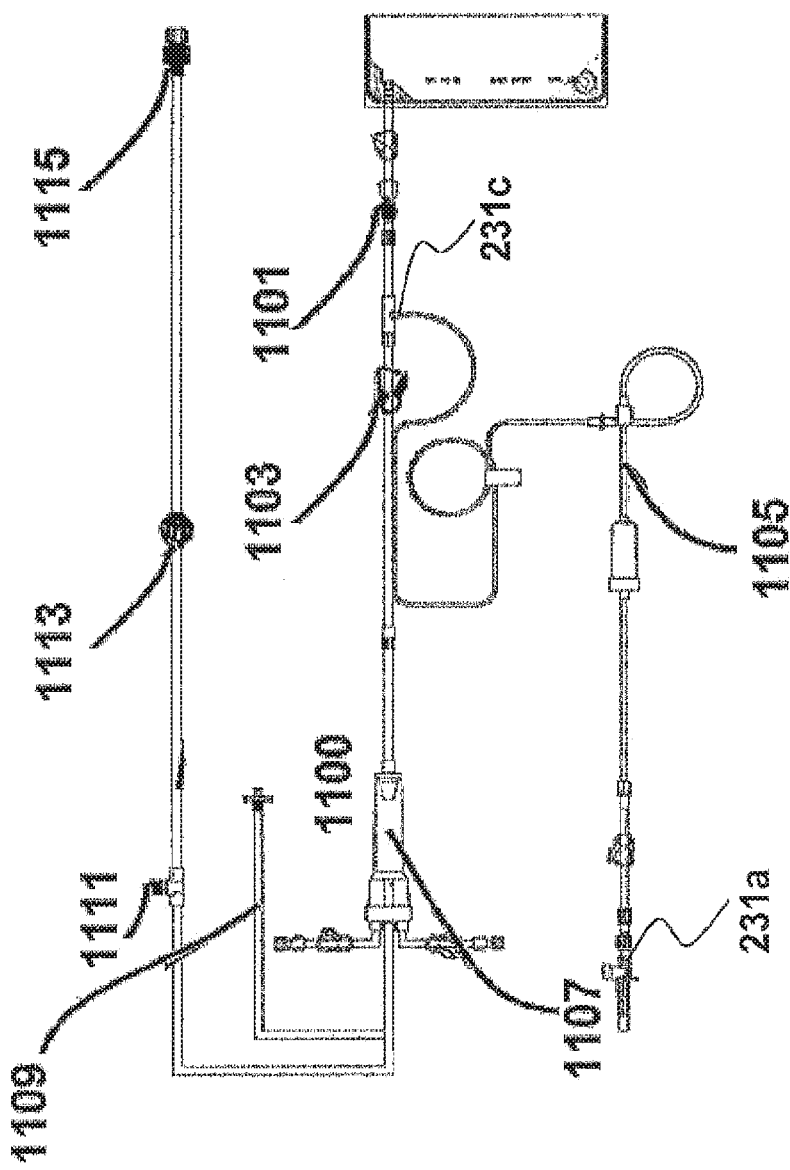

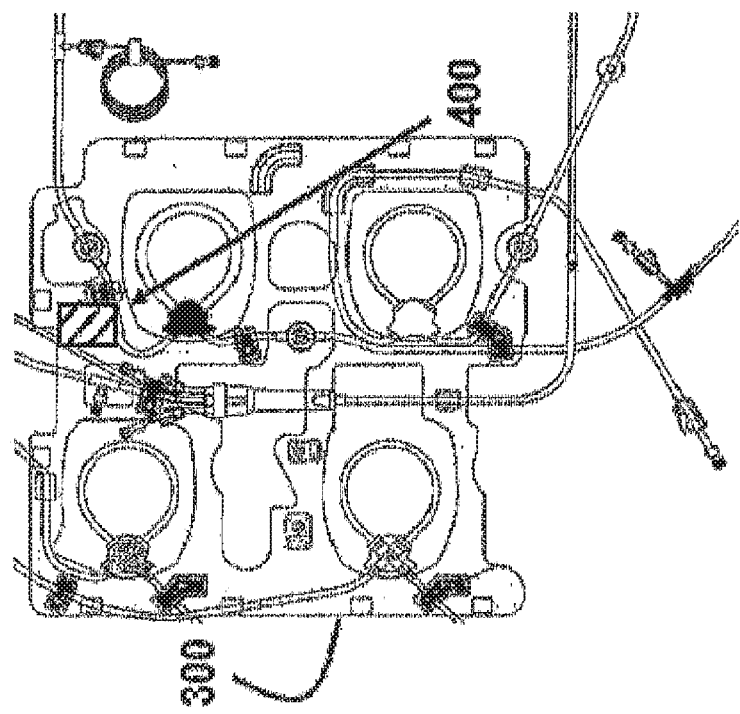
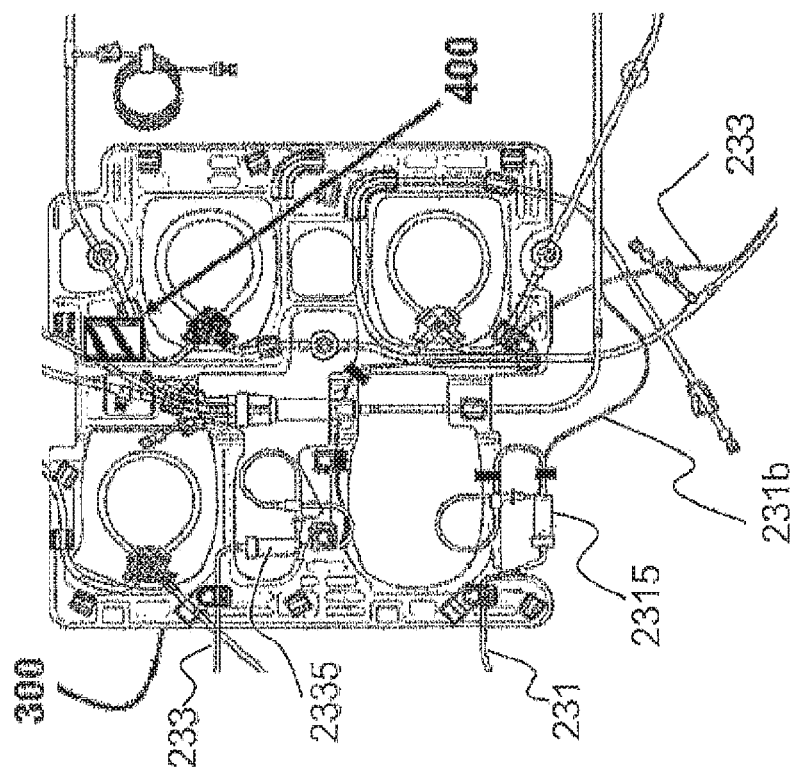

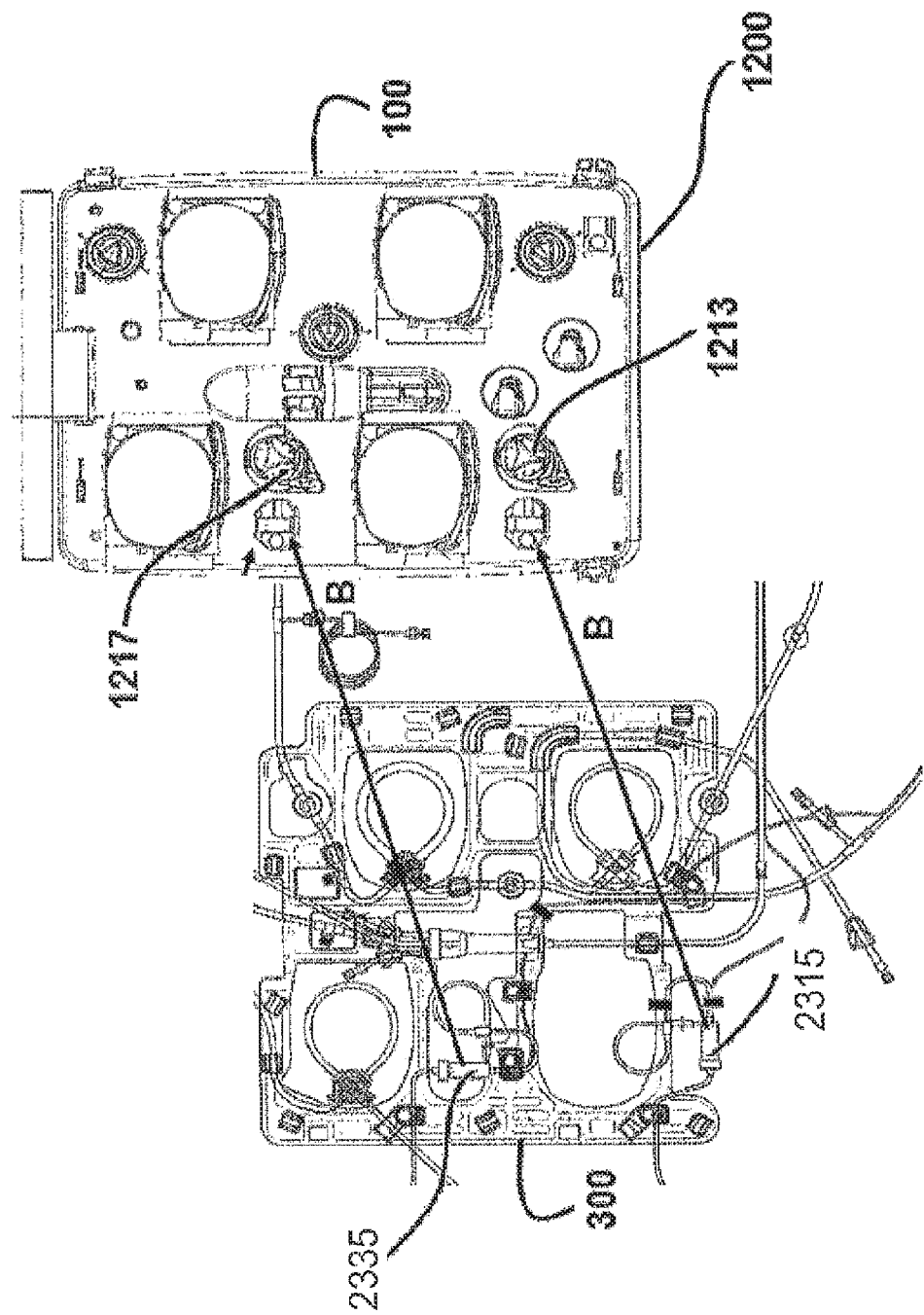

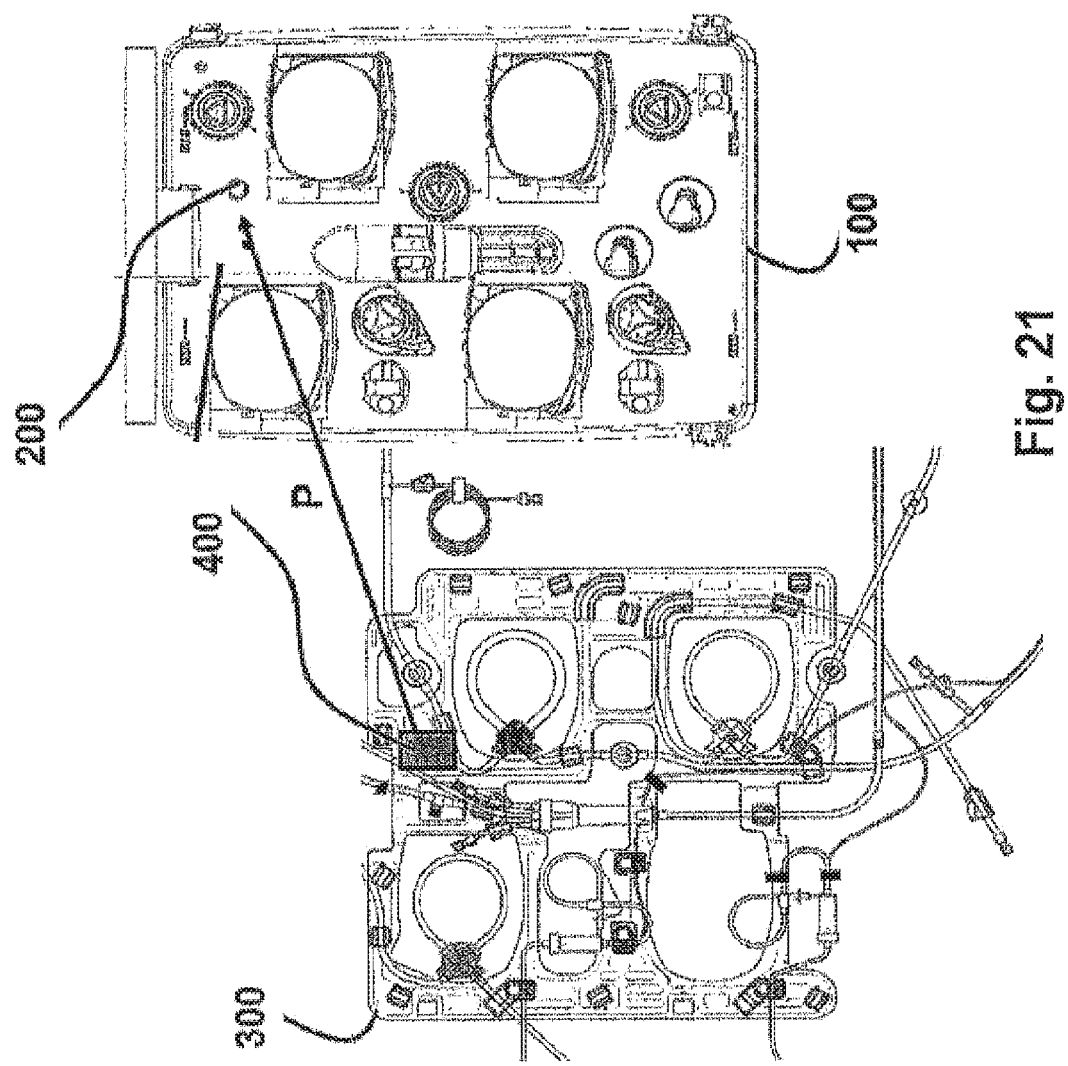

METHOD FOR QUERYING A SPECIFICATION FEATURE OF A MEDICAL TECHNICAL FUNCTIONAL MEANS, A MEDICAL TECHNICAL FUNCTIONAL MEANS, A MEDICAL DEVICE AND A CONTROL UNIT

CROSS-REFERENCE TO RELATED APPLICATIONS

The present application is a continuation application of and claims priority to U.S. application Ser. No. 13/352,843, filed on Jan. 18, 2012, which claims priority to, and the benefit of, U.S. Provisional Application 61/433,533 filed on Jan. 18, 2011, and German Patent Application DE 10 2011 008 856.3 filed on Jan. 18, 2011. The contents of each aforementioned application is incorporated herein by reference in its entirety.

FIELD OF THE INVENTION

The present invention relates to a method for querying a specification feature arranged in, at or on a medical technical functional means. The invention further relates to a medical technical functional means, a medical device and a control unit. Furthermore, the present invention relates to a digital storage medium, a computer program product and a computer program.

BACKGROUND OF THE INVENTION

Medical technical functional means are regularly suitable for being used in certain treatments. This suitability can be identified by means of a specification feature located on the functional means.

One object of the present invention is to provide a method by means of which safety may be enhanced in that, in performing a treatment using a medical technical treatment apparatus, a medical technical functional means is used which is actually apt therefor and not a functional means which is not apt or not sufficiently compatible. Furthermore, a medical technical functional means usable for this purpose, a suitable medical technical treatment apparatus, a suitable control unit, a suitable digital storage medium, a suitable; computer program ID product and a suitable computer program are included herein.

All advantages obtainable by means of the method according to the invention may in certain embodiments according to the invention undiminishedly also be achieved by means of the medical technical functional means according to the invention and/or by means of the medical device according to the invention and/or by means of the control unit according to the invention. In some embodiments according to the invention, this also applies for the digital storage medium according to the invention, the computer program product according to the invention and the computer program according to the invention.

SUMMARY OF THE INVENTION

The method, according to the invention is suited, and provided or intended for querying a specification feature arranged in, at or on a medical technical functional means. The method comprises querying the specification feature by means of a medical device functionally coupled to or to be coupled to the medical technical functional means or by means of a device or means being arranged in signal transmission with the medical technical treatment apparatus.

The medical technical functional means according to the invention (in the following also shortly referred to as: functional means) comprises at least one specification feature marking or identifying at least one, particularly specific or precise or concrete medical technical function or suitability of the medical technical functional means. Thereby, the specification features is arranged in, at or on the medical technical functional means and is provided or intended, suited and/or configured to be queried by means of a medical device functionally coupled to or to be coupled to the medical technical functional means or by means of a device or means being arranged in signal transmission with the medical technical treatment apparatus.

The medical device according to the invention (hereafter referred to as: treatment apparatus) comprises at least one detection device and/or is connected to one such detection device or is arranged in signal transmission relation with one such detection device. The detection device is suited or apt, provided or intended and/or configured for detecting the at least one specification feature marking or identifying at least one function of the medical technical functional means.

The control unit according to the invention is suited or apt and provided or intended and/or embodied or designed and/or configured for performing the method according to the invention.

A digital storage medium according to the invention, in particular in form of a disc, a CD or a DVD, comprising electronically readable control signals may interact with a programmable computer system such as to prompt the execution of the technical steps of a method according to the invention.

Thereby, the execution of all, a few or some of the technical steps of the method according to the invention may be prompted.

A computer program product according to the invention comprises a program code stored in a machine readable storage medium for prompting the execution of the technical steps of the method according to the invention when executing the computer program product on a computer.

The term "machine readable storage medium" as used herein in certain embodiments of the present invention refers to a storage medium comprising data interpretable by means of software and/or hardware. The storage medium may be a data medium such as a disc, a CD, DVD, a USB flash drive, a flash card, a SD card, and the like.

A computer program according to the invention comprises a program code for prompting the execution of the technical steps of a method according to the invention when executing the computer program on a computer.

For the computer program product according to the invention and for the computer program according to the invention it applies as well that the execution of all, a few or some of the technical steps of the method according to the invention are prompted.

BRIEF DESCRIPTION OF THE DRAWINGS

FIG. 15 schematically shows a return line for a calcium and citrate treatment.

FIG. 16A schematically shows a first type of cassette comprising components of a calcium-citrate tubing set.

FIG. 16B schematically shows a second type of cassette not comprising any components of a citrate-calcium tubing set.

FIG. 20 schematically shows the insertion of drip chambers of a functional means at the treatment apparatus.

FIG. 21 schematically shows the detection of the specification feature of the functional means by means of the treatment apparatus according to the invention or by means of the detection device thereof.

DETAILED DESCRIPTION OF THE INVENTION

Figure 1:
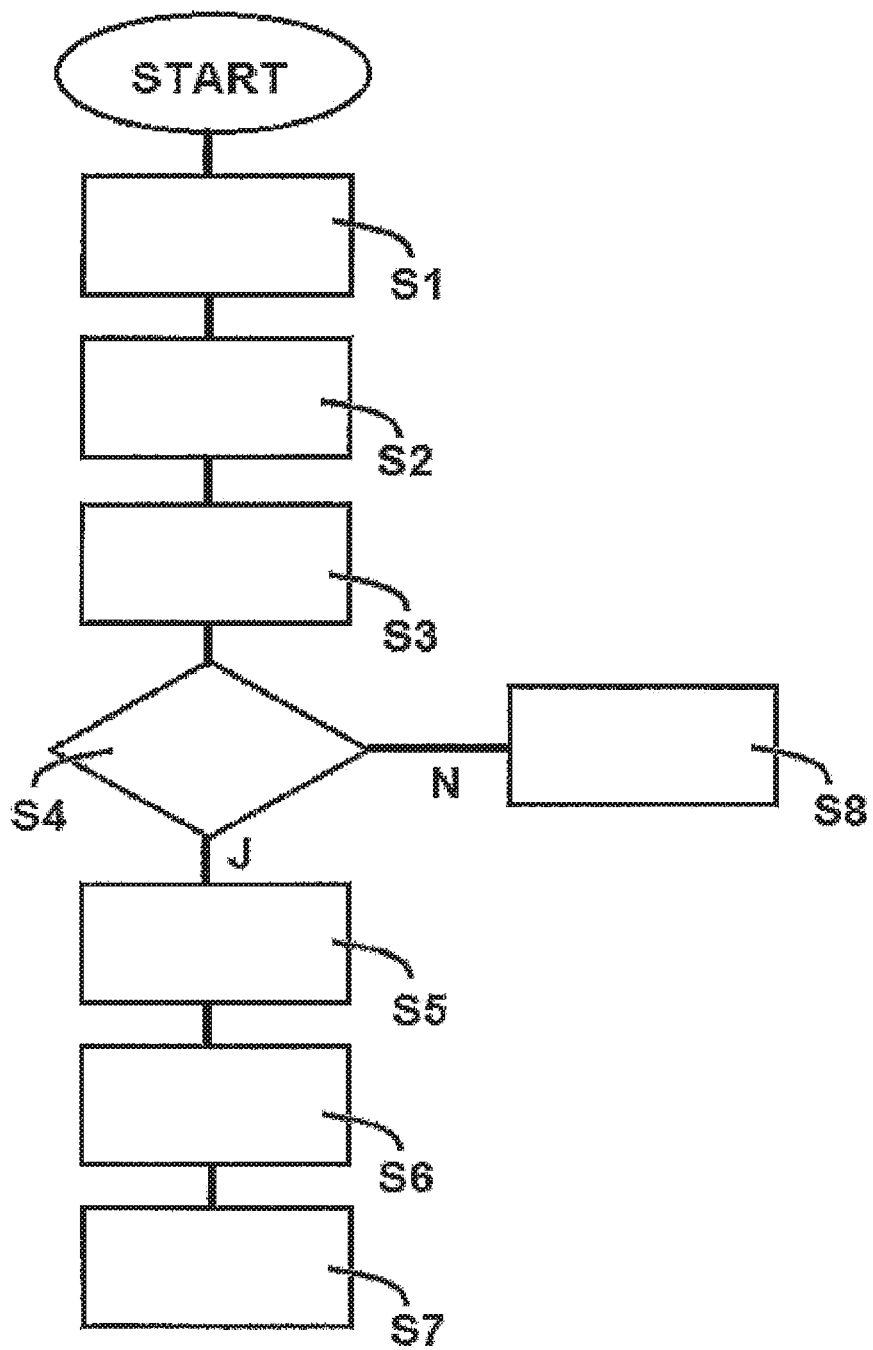
FIG. 1 shows a flow chart of a method according to the invention.

Embodiments according to the invention may comprise a few, some or all of the following features in any arbitrary combination thereof and therewith.

In certain embodiments of the present invention, "querying" refers to ascertaining or determining and/or obtaining and/or gaining or gathering evidence and/or information or data or a statement, or the like about or with respect to the specification feature.

In some embodiments, such evidence, information or data or statements refer to the presence or, however, the non-application or absence of the specification feature itself, or of a certain state, a certain feature, or a certain design or embodiment, or the like, of the specification feature.

In some embodiments, such evidence, information or data or statements refer to a specific or certain, predetermined, defined, desired and/or required quality, quantity, characteristic or specification and/or property, and the like of the specification feature.

In certain embodiments of the present invention, the specification feature marks or identifies or characterizes a function or a suitability for an application or use (or several functions or suitability for different uses as well) of the functional means. In those embodiments, querying the specification feature refers to querying of the at least one function or suitability of the functional means.

In certain embodiments, the specification feature is suited or apt, provided or intended and/or configured for being detected or queried about its information concerning the specifying function (or functions) of the functional means by means of the treatment apparatus or by means of a device or means, being arranged or connected in signal transmission with the treatment apparatus. The treatment apparatus may specifically be prepared or configured for being able to detect or query the specification feature in its concrete design or embodiment.

The terms function and suitability are in certain embodiments to be understood to be identical and/or interchangeable.

In certain embodiments of the present invention, a function or suitability of a medical technical functional means refers to the ability or capability of the medical technical functional means to be able to perform a certain operation, process or procedure, and the like, in particular in the course of or in association with a medical treatment, or to be able to offer a certain usability or benefit.

In certain embodiments, the medical technical functional means is constructed and/or provided or intended and/or designed or embodied for performing a certain operation, process, procedure, etc.

The term "functionally coupling" or "functionally coupled" as used herein in certain embodiments of the present invention refers to the generation or establishment of an operative connection between elements. Without being limited to the operative connections mentioned below, examples of appropriate operative connections include electrical, electronic, mechanical, pneumatic, magnetic, inductive, optical, flow-relevant, and the like, connections.

In certain embodiments, a functional coupling of the functional means with the treatment apparatus refers to an arrangement of the functional means and of the treatment apparatus such that, the treatment apparatus would not be able to perform certain or essential treatment options when lacking such a functional connection.

A device or means connected with the treatment apparatus in signal transmission is, in certain embodiments of the present invention, arranged in signal transmission communication (using physical contact or in a contactless manner) with the treatment apparatus.

The signal used for this may be radio signals, infrared signals, signal using blue tooth, radio waves, electric signal, and the like. These examples are in no way to be understood as limitations.

In certain embodiments, a signal refers to transmitted information about the specification features having been queried, or implies or allows conclusions about it.

Thereby, the signal may be any appropriate kind or type of signal such as an analogue signal, a digital signal, and the like, combinations, mixtures, etc.

Querying the specification feature by means of the treatment apparatus or by means of a device connected in signal transmission with the latter is, in certain embodiments, performed by means of a control unit, a CPU, or the like of the treatment apparatus.

In certain embodiments according to the invention, the specification feature is designed or embodied as an identification mark or label and/or comprises at least one identification mark or label or a tag.

Merely exemplarily and in a non-limiting way, examples of appropriate identification marks or labels include dielectric media, metallic objects, conductors, permanent magnets, oscillating circuits, supports or top frames or protrusions or recesses or grooves, apertures/optics, reflecting and/or light-absorbing and/or light-scattering objects, colored objects, barcodes/patterns, polarizing objects, damping or absorbing objects or oscillation enhancing objects.

In certain embodiments, the specification feature is designed or embodied as a barcode, a dot matrix code, an RFID chip or a color label.

Arbitrary combinations of the identification marks or labels mentioned herein and/or further appropriate labels or identification marks are encompassed by the present invention as well.

The specification feature may be connected releasably or also unreleasably, in particular unreleasably during the coupling procedure of the functional means and the treatment apparatus and/or during the querying procedure of the specification feature, to the functional means or attached in, at or on the functional means.

In certain embodiments, the specification feature is provided or intended for being fixed or attached to or at the functional means by means of sticking, printing, covering, dying, staining, engaging, snapping or clipping, and the like or is fixed or attached in such a way.

The specification feature may or may not be arranged on a support. The specification feature may be arranged or fixed or attached to, on or at the functional means directly. The specification feature may be part of the functional means.

In embodiments in which the specification is or will be fixed or attached in, on or at the functional means by using a support, the support may be selected to be transparent or opaque. Otherwise, it may comprise an underground having colors differing from the colors of the functional means or elements thereof.

In certain embodiments of the present invention, the specification feature is provided or intended for marking or characterizing or identifying an extracorporeal blood tubing set or a certain or specific design or embodiment or applicability of the extracorporeal blood tubing set. Examples of such designs or embodiments or applicabilities of the extracorporeal blood tubing set comprise a design or embodiment or applicability for certain medical purposes such as a blood treatment, e.g. hemodialysis, hemofiltration or hemodiafiltration, with or without using the addition of substitute liquid and, optionally, the addition of at least one anticoagulant and/or further blood additives, and the like.

In some embodiments, the method according to the invention comprises selecting a medical treatment option at the treatment apparatus.

In certain embodiments of the present invention, a treatment option refers to a possible treatment (in several cases one possible treatment out of several different possible treatments), an alternative treatment, a certain treatment process, a course of steps or processes, each relating to a treatment, for example, a blood treatment.

In some embodiments of the present invention, "selecting a treatment option" refers to determining or ascertaining a specific treatment option out of a plurality or multiplicity of different treatment options that can be performed by means of the treatment apparatus.

The selection may be performed manually by inserting or inputting the desired and/or required treatment option into the treatment apparatus or keying the treatment option with the help of an input device or means, suited and provided or intended for this purpose, e.g. a keyboard, a mouse, a push button, and the like, e.g. by a person having the respective authority and/or qualification.

The selection can be done automatically or automatedly based on or subsequently after the pre-processing of the treatment hitherto.

Selection may be done before, during or after querying the specification feature.

The selectable treatment options may be stored or will be stored in the treatment apparatus, for example, in a storage medium of the treatment apparatus.

In certain embodiments, the method according to the invention comprises contacting and/or connecting the functional means with the treatment apparatus or with the detection device of the treatment apparatus.

In certain embodiments of the present invention, "contacting" and/or "connecting" refers to spatially arranging or approximating the functional means and the treatment apparatus with respect to each other. Both procedures serve to query or facilitate querying the specification feature. In contrast to the term "(functionally)" coupling, contacting or connecting the functional means and the treatment apparatus is here to be understood as a mere approximation, for example, in form of bringing together or in form of mechanically connecting the two elements. Establishing a final operative connection is not required for this purpose, however, it is not to be excluded as well.

In certain embodiments, the spatial arrangement of the functional means and of the treatment apparatus allows or serves to query the specification feature by means of the treatment apparatus or by means of a corresponding device or means making use of the proximity that has been generated.

In certain embodiments, the method according to the invention encompasses detecting the specification feature by means of the treatment apparatus or by means of a detection device connected in signal transmission with the treatment apparatus.

In certain embodiments of the present invention, a detection device refers to a means or device suited and provided or intended and/or designed or embodies for detecting and/or measuring the specification feature (or several specification features) of the medical technical functional means.

The detection device is arranged or provided at or on the treatment apparatus or is built or installed therein. In certain embodiments, the detection device is a separate element; in other embodiments, the detection device or a part or section thereof is part of the treatment apparatus, e.g. part of the treatment apparatus's housing.

In certain embodiments, the detection device is designed or embodied and/or provided or intended for generating or prompting or inducing or effecting the measurement signal desired and/or required for detecting and/or measuring the specification feature by itself.

In some embodiments, the detection device is designed or embodied or (physically) connected with or is operatively connected with a signal generation device or means suited, provided and/or configured for this purpose.

Appropriate signal generation devices or means comprise permanent magnets, oscillators, capacitors, power supply units, heat sources, particle emitters, lasers, light sources such as white light LEDs or RGB LEDs (i.e., red, green and blue light emitting LEDs, LED means: light emitting diode), IREDs (i.e., infra red emitting diode), further or other light sources, piezoelectric elements, or the like.

Appropriate measurement signals to be detected for detecting or measuring the specification feature include optical measurement signals such as intensity, frequency (for example, radio frequency), wave lengths, light (such as reflected light), electric measurement signals such as voltage, current, resistance, capacity, inductivity, electric fields, magnetic fields, mechanical measurement signals (such as force, pressure, path), magnetic measurement signals (such as magnetic field strength, magnetic field measurement, magnetization), acoustic measurement signals (such as sound pressure, sound velocity) and/or chemical measurement signals, and the like.

Appropriate detection device include means measuring or detecting optical or opto-electronic effects, capacitative effects, induction or absorption, light signals (color sensors or white light sensors), reflection/transmittance, thermal effects, chemical effects, and further more.

In some embodiments, the detection device detects an effect, the detection device has initiated by itself at the functional means or at the specification feature in order to detect the specification feature; this effect may be a Hall effect, a magnetization, a thermal resistance effect/a thermal electrical effect, a piezoelectric/piezoresistive effect, a photo effect, a voltage/current change, an inductive effect, or the like.

In certain embodiments of the present invention, the detection device is designed or embodied as a hall sensor, a (Reed) relay, a volt/amperemeter, a pressure sensor, an electric switch, a thermal detector or thermo couple, a photodiode or a photo resistance.

In certain embodiments of the present invention, the detection device is designed or embodied, as a barcode reader, a scanner, a color sensor such as a LED sensor, a chip reader, or the like, or as a combination thereof, or comprises said items.

In certain further embodiments, the method according to the invention comprises identifying and/or assigning a function associated with the specification feature.

In certain embodiments of the present invention, "identifying" or "assigning" refers to perceiving or realizing, analyzing or interpreting or evaluating, and the like, the specification feature having been detected by means of the detection device; the specification feature detected will be assigned to a function of the functional means specified or given or defined by the specification feature.

In certain embodiments of the present invention, specification features are stored in the treatment apparatus or in a device or means arranged in data transmission therewith, e.g. in a database or a storage medium of the treatment apparatus or of the device—preferably and/or reasonably together with the corresponding functions of the (one or more) functional means that are specified by means of the specification features.

In certain embodiments, identifying and/or assigning the specification feature encompasses comparing the currently detected specification feature by means of the specification features that are stored in the treatment apparatus.

In certain embodiments, the method according to the invention comprises comparing the selected treatment option that has, e.g. been selected at the medical device with respect to the concrete treatment by, e.g. using the keyboard, with the function or suitability having been identified by means of the treatment apparatus by means of the specification feature of the functional means.

In certain embodiments, comparing encompasses checking if the function of the functional means characterized by the specification feature of the functional means conforms to the selected treatment option and/or is at least compatible therewith.

In certain embodiments, comparing includes ascertaining a Statement—and preferably additionally reporting the statement to the person in charge or the user—about the compatibility of the function of the functional means that has been detected by means of the specification feature of the functional means and the treatment option such that a decision about using the functional means in the treatment option or during a treatment may be made.

In other embodiments, comparing comprises inhibiting or preventing the performance of the selected treatment option at the functional means present. In order to inhibit or prevent a performance in case the functional means has been detected or classified as being "inappropriate", a safety function can be provided. Such a safety function can be a power shut-off or a current breaking or something similar.

In some embodiments, comparing encompasses assessing or evaluating the acceptability and/or reliability of using a certain or specific functional means for a certain treatment option or a certain treatment. In certain embodiments, comparing includes ascertaining a suitability or—preferably uncritical—usability of the functional means. This may, for example, be effected by a comparison with data stored, e.g. data stored in table form.

The result of a comparison may be "positive" or "negative", "right" or "wrong", "correct" or "incorrect", or the like.

In case of a positive result of the comparison, i.e., generally after ascertaining a conformity or compatibility between the identified specification feature (and thus the function of the functional means) and the selected treatment option, it is in certain embodiments provided to prepare or prompt or effect the subsequent use of the functional means in or at or in connection with the treatment, apparatus, e.g. by using automated safety queries.

In certain embodiments, the method comprises functionally coupling the functional means with the treatment apparatus if the treatment option and the identified function conform to each other or are at least compatible with each other.

Functionally coupling may encompass connecting and/or approximating, and the like, the functional means and the treatment apparatus while building up or establishing an operative connection such as a mechanical operative connection, a connection for the purpose of signal transmission, an electrical operative connection, and the like. In certain embodiments, functionally coupling serves to prepare a treatment by means of the treatment apparatus using the functional means.

In further embodiments, the method according to the invention comprises starting defined queries with respect to the correct functional coupling and/or the intermediately obtained usability of the functional means in the planned treatment.

In some embodiments of the present invention, a "defined query" refers to a query or control of certain operations or procedures associated with the use of the functional means or of the treatment apparatus.

In certain embodiments, the defined queries are safety queries provided or intended for enhancing the safety of the systems—and thus advantageously the safety of the patient as well.

Queries concerning the functional coupling and/or the usability of the functional means at or on or with the treatment apparatus include queries about a correct fit of the functional means in the treatment apparatus, the correctness of an arrangement of components relative to each other, a correct signal coupling and/or electric connection between two or more components, a correct closure or opening state "closed" or "open" (such as, for example, in the case of tubings or clamps or valves) of the components to be used, in particular before starting the treatment, and further on.

If the result of the comparison mentioned above is negative, the method according to the invention in certain embodiments comprises alerting and/or reporting the deviation between the selected treatment option and the identified function. This may result may arise if the selected treatment option and the identified function do not conform to and/or are not compatible with each other.

Appropriate alarm and/or reporting devices or means provided for this or other purposes, in particular purposes related to or associated with the treatment, may be provided respectively. Examples include one (or more) devices generating acoustic and/or visual alerts or alarms and/or, for example, devices reporting or displaying the alarm or an error or fault or failure or a problem, such as displays, and the like.

The functional means according to the invention is provided or intended for being functionally coupled to a treatment apparatus. It is suited and provided or intended and/or designed or embodied for being used for performing at least one specific or defined function, in particular in the course of or in association with a medical treatment and/or a medical treatment option.

In certain embodiments, the functional means is designed or embodied for being used in or during an extracorporeal blood treatment.

In certain embodiments, the functional means according to the invention comprises or consists of at least one extracorporeal blood tubing set.

In some embodiments according to the invention, the functional means according to the invention comprises or consists of an extracorporeal blood tubing set arranged in a tray or an organizer.

In further embodiments, the medical technical functional means is designed or embodied as a cassette, e.g. as a disposable cassette.

In certain embodiments of the present invention, an "organizer" refers to a device or means provided or intended for receiving and/or handling the medical technical functional means, for example, the extracorporeal blood tubing set, in a more compact way. The extracorporeal blood tubing set and the organizer may build or make up a cassette in a common arrangement or may be referred to as a cassette. Examples of appropriate organizers can be derived from embodiments of the German patent application DE 10 2008 026 915.8 having the title "Faltbare Organizer für Blutschlauchelemente" ("Foldable organizers for blood tubing elements") of the present applicant, the respective disclosure of which is herewith fully incorporated by way of reference.

As used herein, an extracorporeal blood tubing set may be an extracorporeal blood tubing set that is, for example, used in a blood treatment such as a hemodialysis, a hemofiltration, a hemodiafiltration, or the like. It may comprise all components or elements or devices or means desired and/or required for such (or another (blood)) treatment purpose or may be connected with respective components or elements or devices or means. Non-limiting and merely exemplary examples include lines, chambers, tubings, clamps, sensors such as pressure sensors or air bubble detectors, addition devices or means, valves, throttle valves or restrictors, devices or means regulating the flow of fluids such as, for example, blood and/or dialysate and/or substituate, and the like.

In certain embodiments, the functional means comprises at least one calcium addition site and at least one citrate addition site. The calcium and the citrate addition sites are provided or intended for the addition of citrate and calcium solutions or other anticoagulants acting in accordance with the same or a similar active principle into the functional means or into the extracorporeal blood tubing set.

In certain further embodiments, the functional means furthermore comprises at least one heparin addition site. The heparin addition site is provided or intended for the addition of heparin or other anticoagulants acting in accordance with the same or a similar active principle into the functional means or into the extracorporeal blood tubing set.

In addition to heparin and/or calcium and citrate as anticoagulants, further anticoagulants or substances influencing the blood to be treated in the course of or in association with the treatment may be added. Appropriate devices or means may be provided accordingly.

The addition of heparin or calcium and citrate may be effected by using pumps. Respective pumps suited and/or provided therefor are provided in certain embodiments according to the invention.

The medical device according to the invention is suited and provided or intended and/or designed or embodied for performing one or more steps of a medical treatment and/or one or more treatment options in the course of or in association with a medical treatment.

The medical device may be functionally coupleable or coupled with a medical technical functional means or may be provided herefor.

In certain embodiments, the treatment apparatus comprises at least one identification means or device that is suited, provided or intended and/or configured for identifying and/or assigning a function associated with and/or assigned to the functional means by means of the specification feature that has been detected by means of the detection device.

As stated above, in certain embodiments of the present invention, information about a function or suitability of the functional means associated or related with a specific specification feature may be stored or will be stored in the treatment apparatus or in a storage medium thereof.

In certain embodiments, the treatment apparatus further comprises at least one comparison means or device. The comparison device is suited, provided or intended and/or configured for comparing a treatment option that has been selected at the medical device with the function or suitability of the medical technical functional means that has been identified by means of the specification feature.

In some embodiments, the treatment apparatus further comprises at least one querying device suited, provided or intended and/or configured, for performing defined and/or predetermined queries with respect to the correct functional coupling and/or the usability of the functional means in the planned treatment and/or in association with the selected treatment option, or for prompting the performance thereof. Those queries may particularly be safety queries, especially queries predetermined by the manufacturer or queries predetermined or recommended on a legal basis or according to a standard.

In further certain embodiments, the treatment apparatus further comprises at least one alerting means or device and/or one reporting means or device that is provided or intended for alerting or reporting in case of a non-compatibility of the specification feature or of the function of the functional means or of the functional means itself and of the treatment apparatus or of the selected treatment option. This may particularly be reasonable and/or desired and/or required in cases in which a functional means that does not conform to the selected treatment option has been chosen and was erroneously connected with the treatment apparatus. An alert—in particular an alert that is released or issued in due time before functionally coupling the functional means to the treatment apparatus or even more before starting the treatment—may, in certain embodiments, advantageously contribute to avoiding an unplanned use of the functional means and to thus advantageously increase the patient's safety.

Further alerts and/or reports relating to other situations associated with a treatment may be provided as well as the respective devices or means.

The control unit according to the invention comprises at least one device or means or is functionally coupled to and/or connected in signal transmission with a device or means selected from a group comprising or consisting of a detection device, an identification means, a comparison means, a querying device, an alert means and a reporting means.

Certain embodiments according to the invention comprise one or more of the following advantages.

The present invention provides a method for automatically querying a specification feature of a functional means.

One advantage of the present invention consists of enabling the control of the selection of a medical technical functional means for a specific treatment in addition to the control by the user. Thus, the risk of the results of an incorrect or faulty selection of the functional means to be used by a human being may advantageously be minimized or even excluded.

In certain embodiments, the method according to the invention may advantageously be used during assembling an acute dialysis machine with a disposable blood tubing set that is, for example, provided on an organizer: Such acute dialysis machines that are often able to perform a plurality of several or different functions correspondingly comprising different parameters, treatment procedures, and the like, are mainly often used in emergency cases. For this use, they should be of particular easy and/or clear use or handling. The present invention provides an advantageously simple and reliable method for controlling or monitoring the correct assembling of the blood treatment apparatus with the actually required medical technical functional means.

Thus, according to the invention, it may advantageously be possible to guarantee a high degree of certainty that the functional means is used correctly, also when using a functional means that is designed or embodied in a particular compact way and/or comprises a lot of different functions or a functional means having a high level of integration especially in emergency cases. In turn, this ensures the patient's safety.

In certain embodiments, the present invention advantageously provides a simple and reliable method for enabling a safety-relevant automatic differentiation of functional means, the accidental mix-up of which may be associated with significant risks with respect to the subsequent treatment. For example, in the course of or in association with a blood treatment, two (or even many more) basic types of cassettes or organizers may be used that differ in the tubing set elements provided for the planned anticoagulation method. Usually, those functional means comprise specific branch lines for the respective anticoagulant (e.g. heparin or citrate/calcium) or addition sites designed or embodied otherwise requiring particular consideration before starting the treatment. According to the invention, it is advantageously possible to avoid an accidental use of an inadequate blood tubing set when querying the specification feature as taught by the present invention.

After identifying the specification feature of the functional means, safety aspects specific for the concrete functional means may advantageously reliably be queried.

Thus, in certain embodiments, it is, by means of the present invention advantageously possible to detect the presence of specific lines of a blood tubing set according to their function by means of the specification feature. If one is aware of the presence thereof, a, for example, accidental non-closure thereof that would, however, perhaps be mandatorily required, can be admonished by means of the safety query and can thus be avoided.

When assembling a dialysis machine it may thus particularly be important to lock any branch lines either by means of caps or, e.g. to connect them to respective solution bags so that the ends thereof are secured from the environment. If not, there would be the risk of sucking in ambient air into the extracorporeal blood circuit via branch lines, supply clamps, or the like, that accidentally remain open or that blood could disperse from the extracorporeal blood circuit into the environment. Such a risk could particularly exist with blood tubing sets comprising citrate-calcium addition sites as the calcium line is, for example, arranged at the blood pump's suction side such that air could be sucked in from the environment via an "open" end of the line. Even in the venous line, negative pressure may arise due to the action of the heart with respect to the environment such that, for example, air could be sucked in from the environment via an "open" calcium branch line located there.

By means of the method according to the invention, it may, in certain embodiments, advantageously be possible to avoid an incorrect connection and/or use of a functional means: Basically, it is possible to accidentally use blood tubing sets comprising calcium and citrate lines for an anticoagulation method only operating with a heparin anticoagulation. Calcium and citrate lines that are, however, not present in a heparin tubing set would, however, accidentally unnoticedly remain "open" in case of accidentally inserting a cassette comprising calcium and citrate addition sites when using the treatment option comprising a heparin addition as the machine control would not expect any calcium and citrate lines for the selected treatment, option "heparin addition" and would thus not perform any safety queries, with respect to a treatment option comprising heparin addition. Due to the function of the functional means identified by means of the specification feature, it is, however, according to the invention advantageously possible to prevent such a mistake in advance.

Thus, a risk for the patient and/or a risk of contaminating the environment are advantageously prevented.

In certain embodiments of the present invention, a color label may advantageously be used for identifying or marking the functional means in a particular cost-effective way.

In addition to the possibility of being able to use cost-effective RGB sensors, by using a color label, it may further advantageously be possible to be able of determining with just one look at the color if an appropriate organizer or blood tubing (or an appropriate functional means in general) has been selected. In this way, there is in certain embodiments advantageously provided a further chance of control by the user.

In certain embodiments, coloring or otherwise marking or labeling the package and/or the card of a functional means and being adapted to the coloring or marking of the functional means may further advantageously contribute to a correct selection of the functional means in an easy way.

Identifying the specification feature using color differentiation methods may comprise several advantages as compared to a mere intensity measurement. Those advantages include a higher safety against interfering light, an improved detection or identification of breakdowns or malfunctions, more functionalities in form of differing a plurality of different functional means (that may be embodied or designed in form of disposables), and the like. Additionally, the construction may be less complex and/or may be operated more stable.

In the following, the present invention will be described merely exemplarily with respect to the figures. In the figures, identical reference numerals refer to same or identical elements. The arrows or arrowheads each indicate the flow direction of the respective fluids.

FIG. 1 shows a flow chart of a method according to the invention for querying a specification feature by means of a treatment apparatus or by means of a device or means being arranged in signal transmission therewith.

At first, a medical treatment option is selected on a medical device (step S1).

A medical technical functional means in, at or on which the specification feature is arranged is contacted and/or connected with the medical device or a detection device (step S2). Thereby, it is not decisive if step S1 is performed before, during or after the performance of steps S2, S3, S4 or S5. Step S1 may even be performed after the performance of step S6, however, in a particular case, this may involve unnecessary effort.

The specification feature is detected by means of the medical device or a detection device being external thereto (step S3).

Subsequently, a function associated with the specification feature is identified and/or assigned thereto (step S4).

Now, the treatment option that has been selected in step S1 on the medical device is compared with the function that has been identified in step S4 by means of the specification feature of the medical technical functional means (step S5).

If the treatment option that has been selected in step S1 at the medical device and the function that has been identified in step S4 by means of the specification feature of the medical technical functional means conform to each other or are compatible with each other ("J" for YES), the medical technical functional means and the medical device will be functionally coupled (step S6). This coupling may correspond to a, particularly final, assembling of the treatment apparatus with the functional means.

Then, defined queries concerning the correct functional coupling of the medical technical functional means for the purpose of the planned medical treatment or queries concerning safety aspects will be started (step S7).

If the treatment option having been selected on the medical device and the function having been identified by means of the specification feature of the medical technical functional means do not conform, to each other or are not compatible with each other ("N" for NO), an alert, and/or report about a deviation between the selected treatment option and the identified function or suitability of the functional means differing therefrom is issued (step S8).

Figure 2:
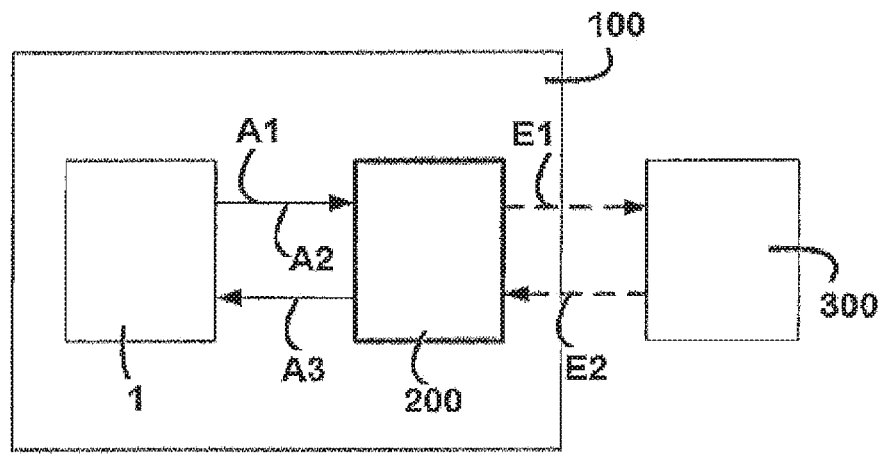
FIG. 2 schematically shows a signal transmission connection between a treatment apparatus according to the invention, a detection device and a functional means.

FIG. 2 schematically shows a signal transmission connection that is generated between a treatment apparatus 100 according to the invention, a detection device 200 and a functional means 300.

The treatment apparatus 100, e.g. an acute dialysis machine, comprises a control unit 1 (hardware of the machine).

As shown in FIG. 2, the control unit 1 functions as an interface between the treatment apparatus 100 and the detection device 200.

Via control unit 1, control signals of the software of the treatment apparatus 100 are sent to the detection device 200 (signal "A1"). As shown in FIG. 2, the detection device 200 is supplied with power by means of the control unit 1 of the treatment apparatus (signal "A2").

For detecting the specification feature of the functional means 300, the detection device 200 emits a signal E1. The information subsequently emitted or issued by the functional means 300 is returned as signal E2 to the detection device 200 and then as signal "A3" to the control unit 1 of the treatment apparatus 100.

Figure 3:
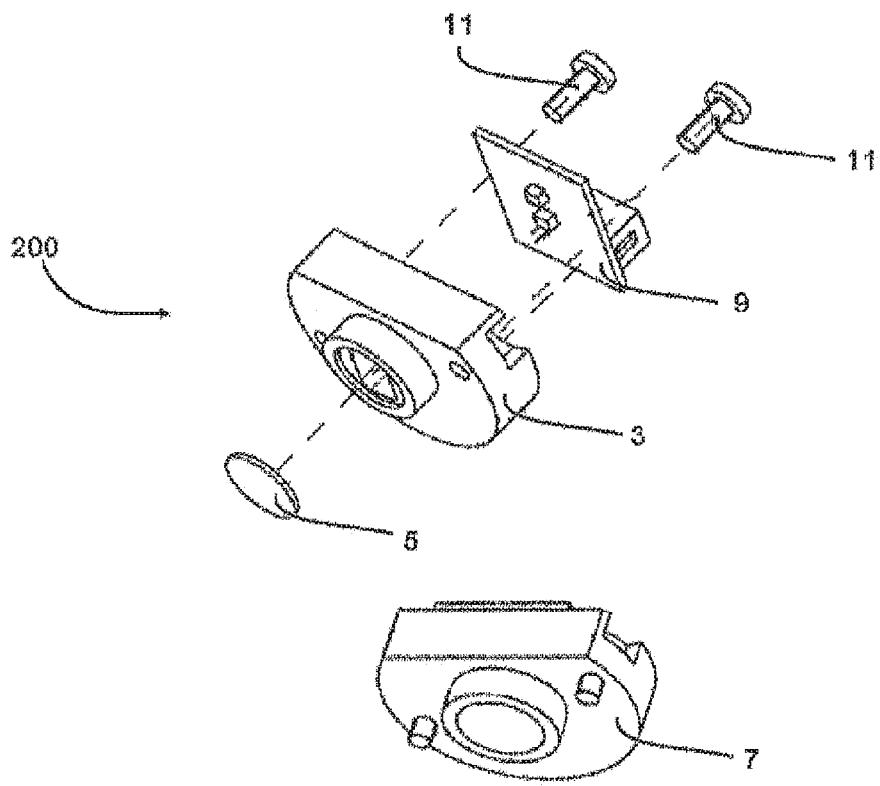
FIG. 3 perspectively shows components of a detection device.

FIG. 3 perspectively shows components of a detection device 200.

In FIG. 3, the detection device 200 is exemplified as a sensor, e.g. as a color sensor.

The detection device 200 comprises a housing 3.

A front panel 5 can be integrated into the housing 3. The housing 3 and the front panel 5 can be covered by means of a cover 7.

As can be seen from the schematic arrangement of the components in FIG. 3, a circuit board 9, e.g. comprising a LED (light-emitting diode) and/or a light-frequency-converter, is arranged in the assembled state of the detection device 200.

The detection device 200 is screwed together with the treatment apparatus (not shown in FIG. 3), e.g. with a machine front of the treatment apparatus, by means of fastening bolts 11.

Figure 4:
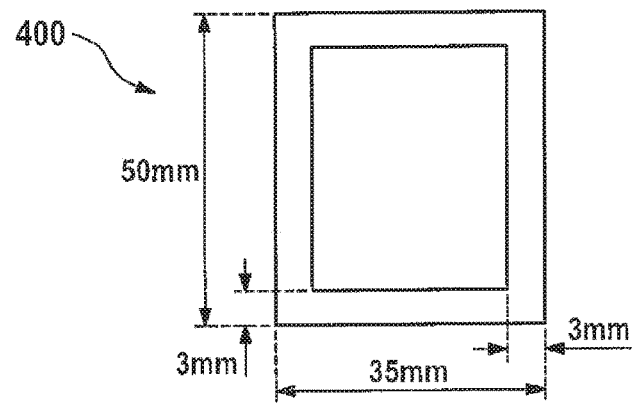
FIG. 4 shows a front view of an exemplary specification feature.

FIG. 4 shows a front view of an exemplary specification feature 400.

The specification feature 400 is attached to the functional means such as an organizer or a "tray" by means of, for example, adhesive bonding.

As shown in FIG. 4, in this embodiment, sufficient sticking or attachment of the specification feature 400 (e.g. a color label) at a functional means (not shown in FIG. 4) can be assured by a width of the adhesive surface for all sides of exemplarily 3 mm. When considering the positional tolerance of the tray of, for example, ±5 mm, there still remains a sufficiently large readable area of the specification feature, as is exemplarily shown in FIG. 4.

The maximum dimensions of a specification feature 400 at a functional means may depend on several factors, for example, on the position of the detection device on the treatment apparatus, and the like. In FIG. 4, the maximum dimensions are 50 mm×35 mm.

Color labels on organizers, cassettes, or the like may be produced in different ways, wherein possible color changes resulting from sterilization and/or age are preferably minimized or anticipated. Examples of attaching a specification feature 400 in, at or on a functional means include printing, covering, dying, staining, applying, e.g. engaging or snapping or clipping a color tag, etc.

Figure 5A:
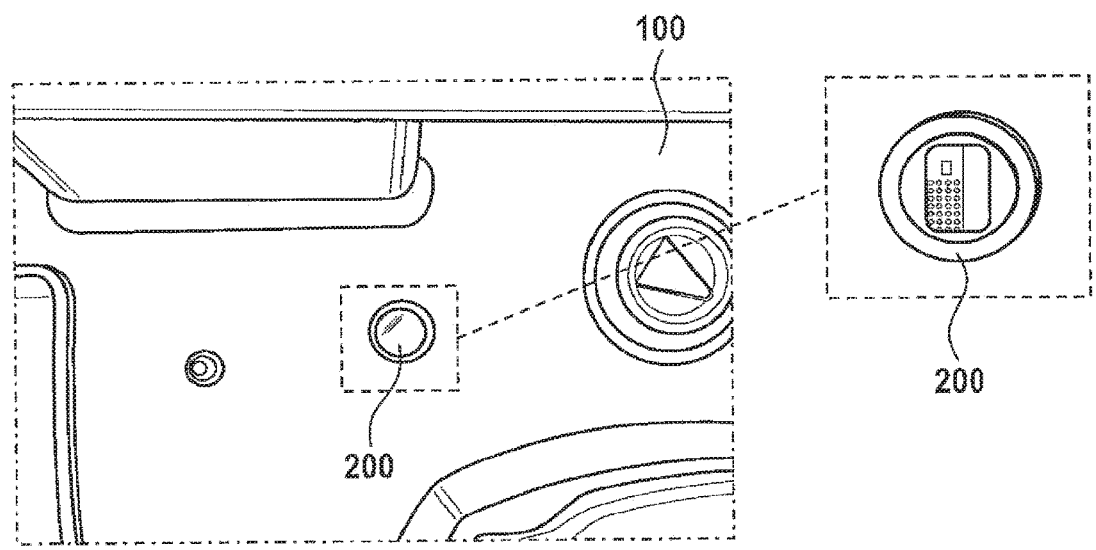
FIG. 5A shows a configuration of the detection device at a treatment apparatus according to the invention.

FIG. 5A shows a detection device 200 arranged on a treatment apparatus 100 according to the invention, the detection device 200 is exemplarily designed as a sensor. To the right of the arrangement, the detection device 200 is shown enlarged.

Figure 5B:
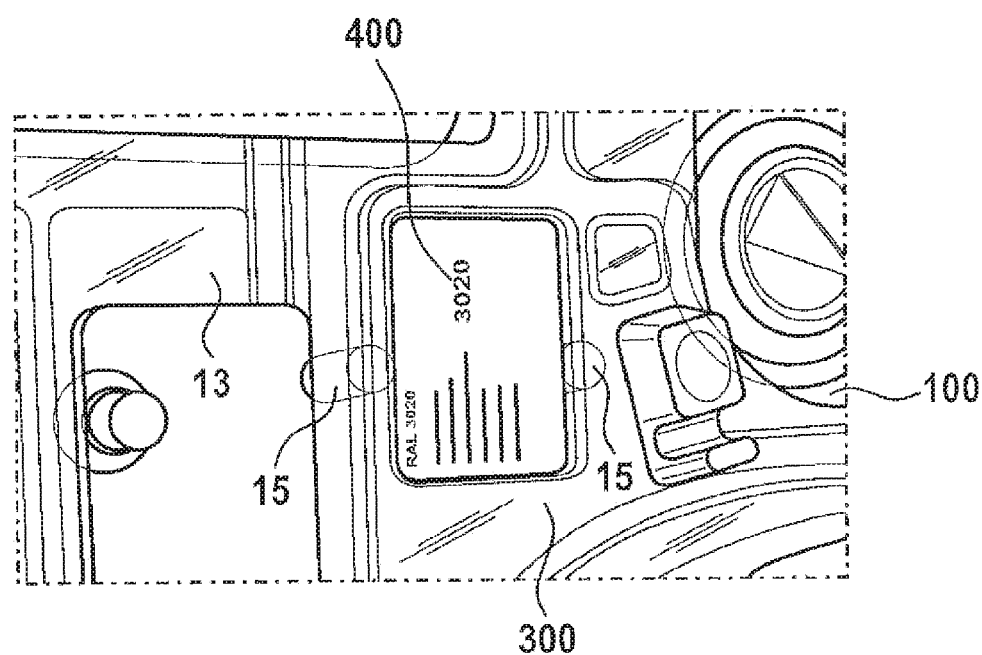
FIG. 5B shows a treatment apparatus according to the invention comprising a functional means arranged thereon.

FIG. 5B shows a treatment apparatus according to the invention 100 at which a functional means 300 according to the invention is arranged.

As shown in FIG. 5B, the functional means 300 comprises a tray or an organizer 13. In some embodiments, the organizer advantageously contributes to positioning the individual components, e.g. lines, tubings, clamps, etc., correctly relative to the treatment apparatus 100.

The arrangement of single components such as of an extracorporeal blood tubing set or a tubing set in a tray or organizer 13 may, in certain embodiments, advantageously facilitate the handling of the extracorporeal blood tubing set.

At or on the organizer 13, e.g. on the organizer's 13 backside, there is arranged a specification feature 400, e.g. a color label.

By means of its concrete design or embodiment, the specification feature 400 is positioned on the organizer 13 in front of the detection device 200 in conformity with the arrangement of the detection device relative to the treatment apparatus in a manner suited for the purpose of detection.

In order to avoid variations of the distance between the specification feature 400 and the detection device (not seen in FIG. 5B, as the specification feature 400 covers it) resulting from different organizers possibly to be used with the blood treatment apparatus, distance rings 15 are provided.

The distance rings 15 may, for example, have a thickness of 0.8 mm each.

The organizer 13 or the "tray" assembled with a blood tubing Set—also referred, to as a cassette—is, in some embodiments, provided or intended for being used in a sterilely form.

The organizer 13 can be assembled with different blood tubing sets, for example, with tubing set elements for different anticoagulation methods, e.g. heparin anticoagulation and/or citrate/calcium anticoagulation ("CiCa.").

In certain embodiments, such anticoagulation methods require specific branch lines at the blood tubing set opening at specific sites into the extracorporeal blood circuit such that, during the treatment, anticoagulants may be added to the blood. In erase of blood tubing sets for the CiCa anticoagulation, a heparin anticoagulation may be provided additionally such that, in some embodiments, branch lines for both anticoagulation methods are provided.

If, after predetermining a selected treatment option comprising citrate-calcium anticoagulation or heparin anticoagulation, neither a yellow label nor a blue label that are expected here exemplarily are identified, an alarm or error message ("improper cassette or organizer" or "problem with color detection of the cassette or the organizer", or something similar) may be issued. In this way, the performance of the treatment using an improper organizer/cassette may be avoided.

The blood treatment apparatus automatically recognizes or identifies a regular case in which, on the one hand, a treatment opt ion comprising citrate-calcium anticoagulation has been pre-selected by means of the machine control and then an, e.g. yellow label has been detected. Subsequently, the machine control automatically performs successive specific safety queries—optionally in combination with corresponding sensors arranged at the insertion sites of the coupling surface. Thus, it is, e.g. ensured that the calcium and citrate lines present are really inserted properly or are secured.

The tubing system that is provided for heparin treatment lacks those components and thus, the said components are not checked for proper insertion by means of the machine control.

If, after predetermining a treatment option comprising citrate-calcium anticoagulation, the expected yellow label is not identified but, e.g. a blue label (blue for heparin) is identified, thus an alarm or error message ("improper cassette/organizer" or something else) and/or an alert may be issued and the performance of the treatment using the improper cassette/the improper organizer may be avoided.

If, after predetermining a treatment option comprising heparin anticoagulation, the expected, e.g. blue label is not identified but, e.g. a yellow label (for citrate-calcium) is identified, thus an alarm or error message ("improper cassette/organizer", "performance of the treatment is not allowed" or something else) may be issued and the performance of the treatment using the improper cassette/the improper organizer may be avoided.

This may be of particular relevance as, due to the predetermination of the heparin anticoagulation, a usual machine control checks a blood tubing set lacking branch lines for a citrate-calcium anticoagulation and thus does not provide any corresponding safety queries for securing potentially open citrate and/or calcium lines.

If, in a further proper case, after having selected a treatment option comprising heparin anticoagulation, the blood treatment machine identifies a blood tubing set comprising, e.g. a blue label, i.e. a blood tubing set organizer or a cassette for heparin anticoagulation alone and without comprising any citrate and calcium lines has been inserted, the machine control, optionally in combination with corresponding sensors at the insertion site of the coupling surface, therefore automatically performs specific safety queries, whereby it may advantageously be ensured that all components present have been inserted properly or are secured properly. Due to the coloring, the control acts on the assumption of a cassette not comprising any branch lines for a citrate-calcium anticoagulation and thus does not provide any corresponding safety queries for securing open citrate and calcium lines.

If the identified cassette fits to or conforms to the pre-selected treatment option, the machine control, optionally in combination with corresponding sensors at the insertion sites, performs specific safety queries, whereby it is ensured that all relevant lines are queried and secured. Otherwise, an alarm or error message and/or an alert ("improper cassette/organizer" or something else) may be issued and/or the performance of the treatment using the improper cassette that has already been inserted may be avoided.

In certain embodiments, it is possible and provided or intended that, even if a tubing system has been identified by the label that does not conform to the selected treatment option, a citrate-calcium treatment is allowed by the treatment apparatus as it is hereby checked for correct-insertion of the (open) citrate and calcium lines. The danger that would arise from these tubing parts can thus be averted.

Figure 6:
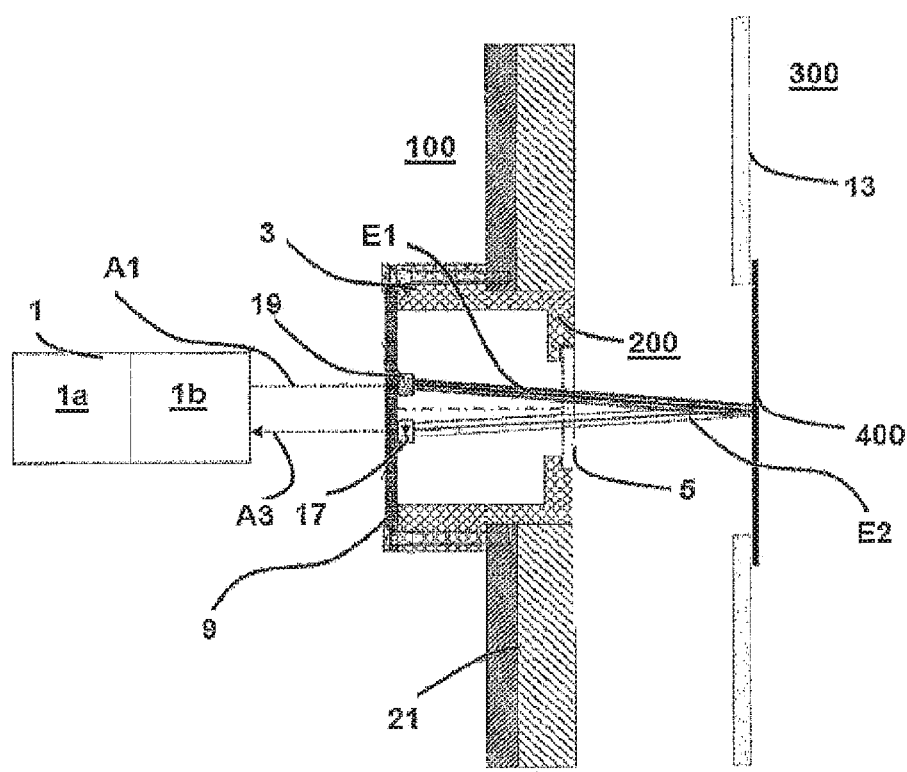
FIG. 6 shows a basic principle of the arrangement and the functionality of the detection device.

FIG. 6 shows a basic principle of the design and the functionality of an exemplary detection device 200. In FIG. 6, the detection device 200 is embodied as a color sensor.

The detection device 200, that is shown in the center of FIG. 6, comprises a light-frequency converter 17 and a RGB LED (red-green-blue light-emitting diode) 19 inside its housing 3.

The light-frequency converter 17 and the RGB LED are arranged on a circuit board 9 of the detection device 200.

The detection device 200 or its housing 3 are arranged on a machine surface of the treatment apparatus 100. As shown in FIG. 6, the housing 3 of the detection device 200 may be integrated into a housing 21 of the treatment apparatus 100.

The front panel 5 of the detection device 200 is in the example of FIG. 6 arranged in a manner flush to the adjacent machine surface of the treatment apparatus 100 whereby advantageously facilitating the cleaning process; however, front panels 5 that are recessed, or protrude from the machine surface may be provided as well.

On the right hand side of FIG. 6, a functional means 300 is shown that is positioned at or—depending on its state of use—in front of the treatment apparatus 100.

The control unit 1 of the treatment apparatus 100 comprises a software component 1a and a hardware component 1b.

For detecting the specification feature 400 by means of the treatment apparatus 100 or the detection device 200 thereof, a control signal A1 is sent from the control unit 1 to the detection device 200. The detection device 200 detects the specification feature 400 by means of light reflection methods and sends the information gained as frequency A3 back to the control unit 1.

A measurement method for detecting the specification feature 400 may, in certain embodiments according to the invention, be performed in the following way by means of using a color sensor (RGB sensor) as the detection device 200 and a color label as the specification feature 400.

For calibrating the detection device 200, if applicable in form of a calibration already done by the manufacturer, each RGB LED (red R, green G, blue B) may be switched on by gating or fading out extraneous light and the corresponding output frequency of the sensor may be measured. The frequency value obtained in this way may reflect the basic frequency of the sensor superimposing the actual measurement value in each measurement process (offset).

First, at the beginning of the measurement process, a frequency measurement is performed with the LED being switched off (~50 ms). Then, the red LED is switched on and about 0.5 s is waited. Before resuming a measurement value as a variable, a delay of about 150 ms is waited such that LED and receiver (specification feature) are present in a defined state. Now, frequency is measured (~50 ms). Then, the red LED is switched off, the green LED is switched on and is waited again (~0.5 s). Frequency is measured (~50 ms). After switching off the green LED, the blue LED is switched on and for example, approximately for another 0.5 s is waited again. Frequency is measured (~50 ms), The blue LED is switched off. Then, for about 0.5 s; is waited. Frequency is measured (~50 ms). Another value for extraneous light is recorded again.

For evaluating the measurement, at first the first and the last frequency measurements without LED are compared to each other (in case of a deviation between these two values, the measurement process would be repeated). The higher value for extraneous light and the lower value for extraneous light should not differ from each other by more than 20%.

Subsequently, the resulting frequencies are calculated. For each color, the offset determined during the manufacturer's calibration process and the frequency value of the first measurement without LED are subtracted from the measurement value.

The factors for the color comparison are calculated by building the factor for green from red/green and for blue from red/blue with respect to the offset values. The factor for red is 1.

For the color comparison, the frequencies are multiplied by the respective factors. The identification of the color is done by comparing quotients of color intensities (R, G, B) with each other within predetermined tolerance intervals.

Red/green, red/blue and green/blue ratios are calculated.

Then, a query is started if the ratios are greater than or less than 1. By comparing with predetermined values, information about the functional means may be gained.

If, for example, a yellow label (e.g. for citrate-calcium) is identified, the red/green ratio is, for example, >2.1. A result of the variable may be true here. At the same time, the red/blue ratio is >1.5. The result of the variable may be true again. Thus the color yellow is identified or recognized.

If a method comprising the addition of citrate-calcium has been selected as the treatment option, congruence between the selected treatment option and the function or suitability of the functional means is determined.

If, however, a method comprising the addition of heparin has been selected as the treatment option, there is no congruence or conformity between the selected treatment option and the function of the functional means. An alert should be issued.

If the red/green ratio is, for example, ≤2.1, a blue label (e.g. for heparin) is identified. A result of the variable may be true here. At the same time, the red/blue ratio is, for example, ≤1. The result of the variable may be true again. Thus, the color blue is identified.

If a method comprising the addition of heparin has been selected as the treatment option, congruence between the selected treatment option and the function or suitability of the functional means is determined.

If, however, a method comprising the addition of citrate and calcium has been selected as the treatment option, there is no congruence or conformity between the selected treatment-option and the function of the functional means. An alert should be issued in this case again.

If, even before starting the color identification, an alarm or error message is issued, a reason herefor could be that the functional means had not been positioned at the treatment apparatus in the right way such that the specification feature cannot be detected by means of the detection device. Optionally, failure notice comprises a corresponding indication.

Figure 7:
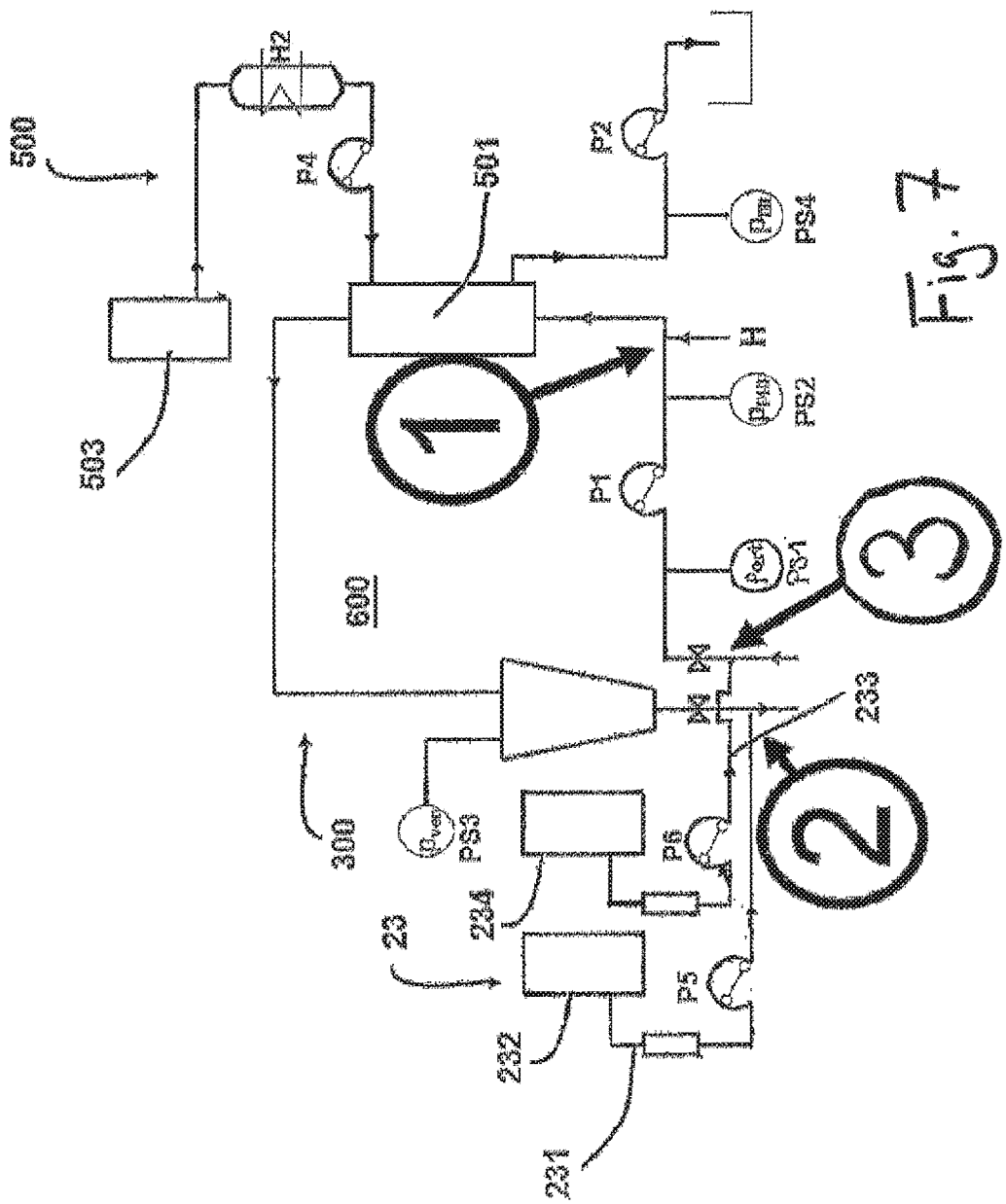
FIG. 7 schematically shows an arrangement of a functional means for performing a blood treatment comprising the addition of citrate and calcium (yellow cassette label).

FIG. 7 schematically shows a configuration of a functional means 300 for performing a blood treatment comprising the addition of citrate at first—or upstream—and later on calcium (relative to a flow of a concrete erythrocyte moved extracorporeally)—or more downstream.

Anticoagulation lines for calcium and citrate are indicated on the machine-sided coupling surface of the functional means 300 at a defined position by means of a specification feature, e.g. in form of a yellow color label such as a sticker. This is, in certain embodiments, independent from providing a heparin line additionally.

The functional means 300 represents an extracorporeal blood circuit or blood tubing set for a blood treatment of a patient, e.g. a hemofiltration.

On the right side of FIG. 7, a dialysate circuit 500 comprising a dialyzer 501 and a source 503 for filtrate or dialysate is shown.

The part indicated by "600" represents the blood circuit. The blood circuit 600 is substantially or completely part of the functional means 300.

The functional means 300 shown in FIG. 7 schematically represents an extracorporeal blood tubing set provided for a dialysis (CVV-HD=continuous venous to venous hemodialysis) comprising citrate-calcium tubing elements 23. The citrate-calcium tubing elements 23 comprise a first supply line 231 for supplying calcium from a calcium source 232 by means of a pump P5 as well as a second supply line 233 differing therefrom for supplying citrate from a citrate source 234 by means of a pump P6.

The supply lines 231 or 233 open into the extracorporeal blood tubing set at the connection sites denoted by ② or ③ each representing branch lines of the extracorporeal blood tubing set having open connection sites (open as in case of a calcium and citrate addition, introduction of calcium or citrate should be done at the corresponding position into the extracorporeal blood tubing set).

As shown in FIG. 7, calcium addition is done behind, or downstream of the dialyzer 501. If the connection site ② should accidentally remain open, there would be the risk of dissipating extracorporeally treated blood at the connection site ② from the extracorporeal blood tubing set into the environment.

As shown in FIG. 7, citrate addition is done in front of or upstream of the dialyzer 501. If the connection site ③ should accidentally remain open, there would thus be the risk of sucking in air into the extracorporeal blood tubing set by means of the blood pump P1 and thus to optionally introduce air into the patient connected with the extracorporeal blood tubing set.

In some citrate-calcium cassettes or tubing sets, a heparin addition site is provided additionally; in other citrate-calcium cassettes or tubing sets, it is not.

A heparin addition site H is in FIG. 7 indicated as connection site ①. In a cassette comprising citrate and calcium addition, the connection site ① is, for example, secured by means of a non-return valve. Thus, a potential risk due to an open connection site ① may advantageously be excluded.

As compared to, for example, a heparin tubing set, as stated, a citrate and calcium tubing set additionally comprises open connection sites ② and ③ via which blood could, escape and air could enter if they were not closed accidentally. Therefore, they have to be closed reliably.

The terms p(art) or PS1, p(PHF) or PS2, p(ven) or PS3 refer to pressure sensors for detecting the blood pressure at the respective sites within the extracorporeal blood tubing set. Further, the terms p(filt) or PS4 refer to pressure sensors for detecting the dialysate pressure at the respective sites within the extracorporeal blood tubing set.

Figure 8:
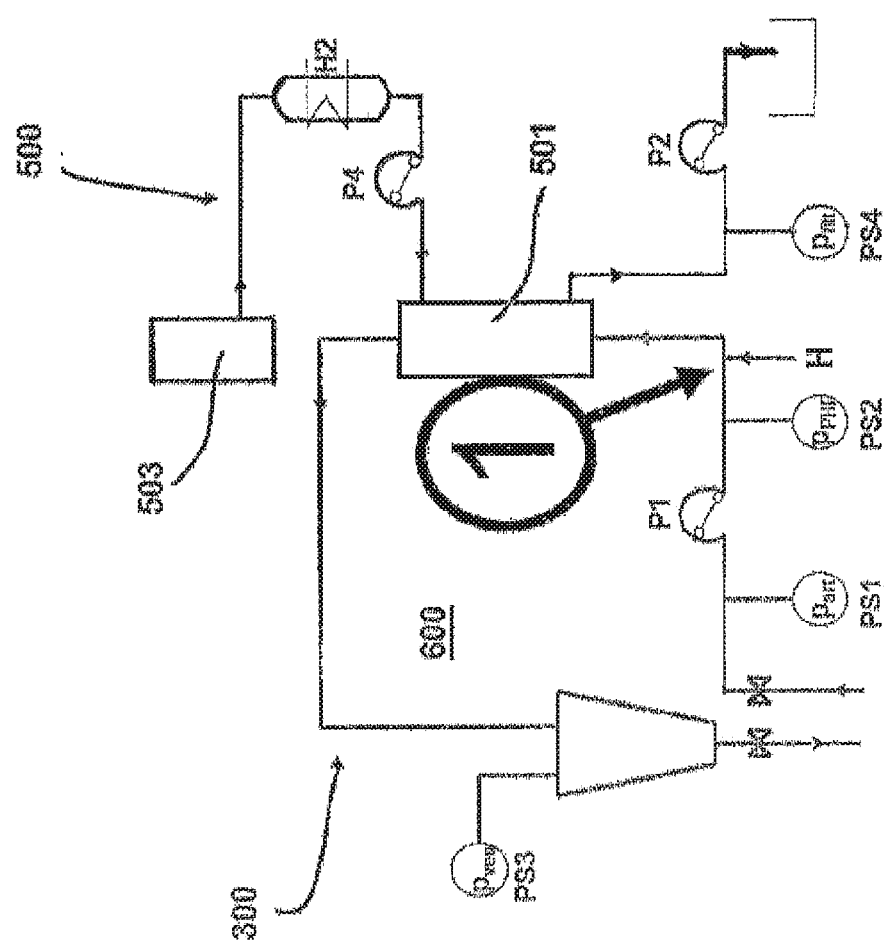
FIG. 8 schematically shows an arrangement of a functional means for performing a blood treatment comprising the addition of heparin (blue cassette label).

FIG. 8 schematically shows a configuration of a functional means 300 for performing a blood treatment comprising heparin addition.

In certain embodiments, cassettes provided for heparin anticoagulation alone comprise, for example, a blue color label, e.g. a blue sticker ("heparin=blue") for differentiating the cassette from a cassette comprising citrate and calcium addition.

In this way, nursing staff may advantageously already optically or visually get a first hint about the suitability of the respective cassette for specific treatment options.

The arrangement of the functional means 300 in FIG. 8 substantially corresponds to the one shown in FIG. 7, however, no citrate and calcium tubing element is present. The treatment apparatus identifying a blue color label expects a set without any open citrate and calcium connection site and would not check such sites.

In the following FIGS. 9 to 13, the references "in" and "out" in the FIGS. refer to inflow ("in") or outflow ("out") of the respective fluid into the functional means or out of the functional means.

Figure 9:
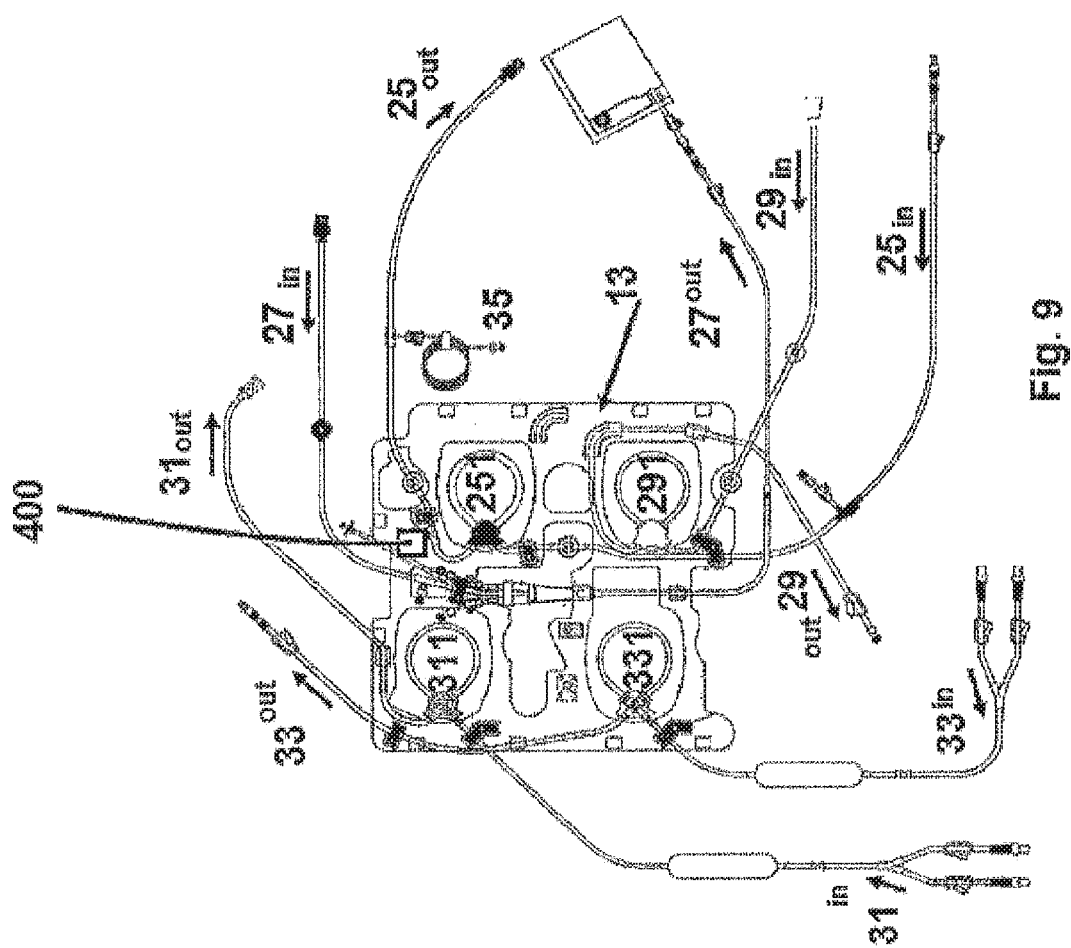
FIG. 9 schematically shows a tubing set comprising a heparin addition site.

FIG. 9 schematically shows a tubing set comprising a heparin addition site.

The heparin tubing set arranged on an organizer 13 and identified by means of a specification feature 400, e.g. a blue color label, comprises a supply line 25in and 23out for blood extending from the patient to the filter, e.g. a dialysis filter. The tubing set further comprises a return line 27in and 27out for blood extending from the filter (not shown in FIG. 9) to the patient (not shown in FIG. 9). Furthermore, a filtrate line referred to as 29in and 29out is provided.

A dialysate line 31in and 31out for dialysate or dialysis fluid extending from a solution bag (not shown in FIG. 9) to the filter or a connector is also provided. Furthermore, a substituate line 33in and 33out for transporting substitution fluid or substituate from a solution bag (not shown in FIG. 9) to the connector in the supply line 25 or the return line 29 is provided.

A heparin addition site 35 is provided for adding heparin upstream the filter into the blood tubing line 25out and downstream the blood pump 251.

In FIG. 9, furthermore a filtrate pump 291, a dialysate pump 311 and a substituate pump 331 are represented.

Figure 10:
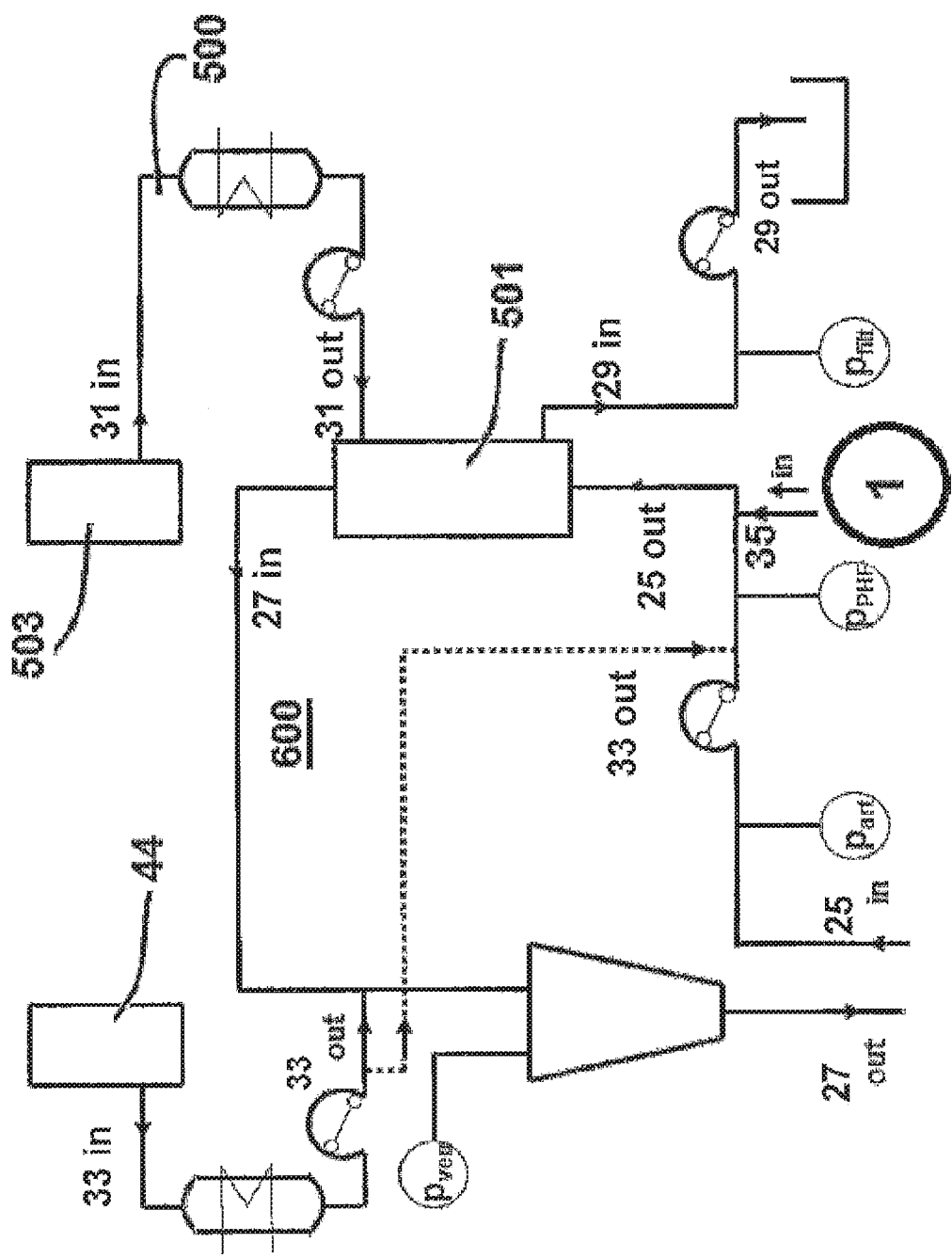
FIG. 10 schematically shows a diagram of an arrangement for performing a blood treatment comprising the addition of heparin.

FIG. 10 schematically shows a flow chart of an arrangement for performing a blood treatment comprising the addition of heparin by using a heparin tubing set such as specified in FIG. 9.

FIG. 10 shows the lines of the extracorporeal blood circuit 600 and of the dialysate circuit 500. Substitute liquid is supplied from a source 44 for substituate liquid.

Figure 11:
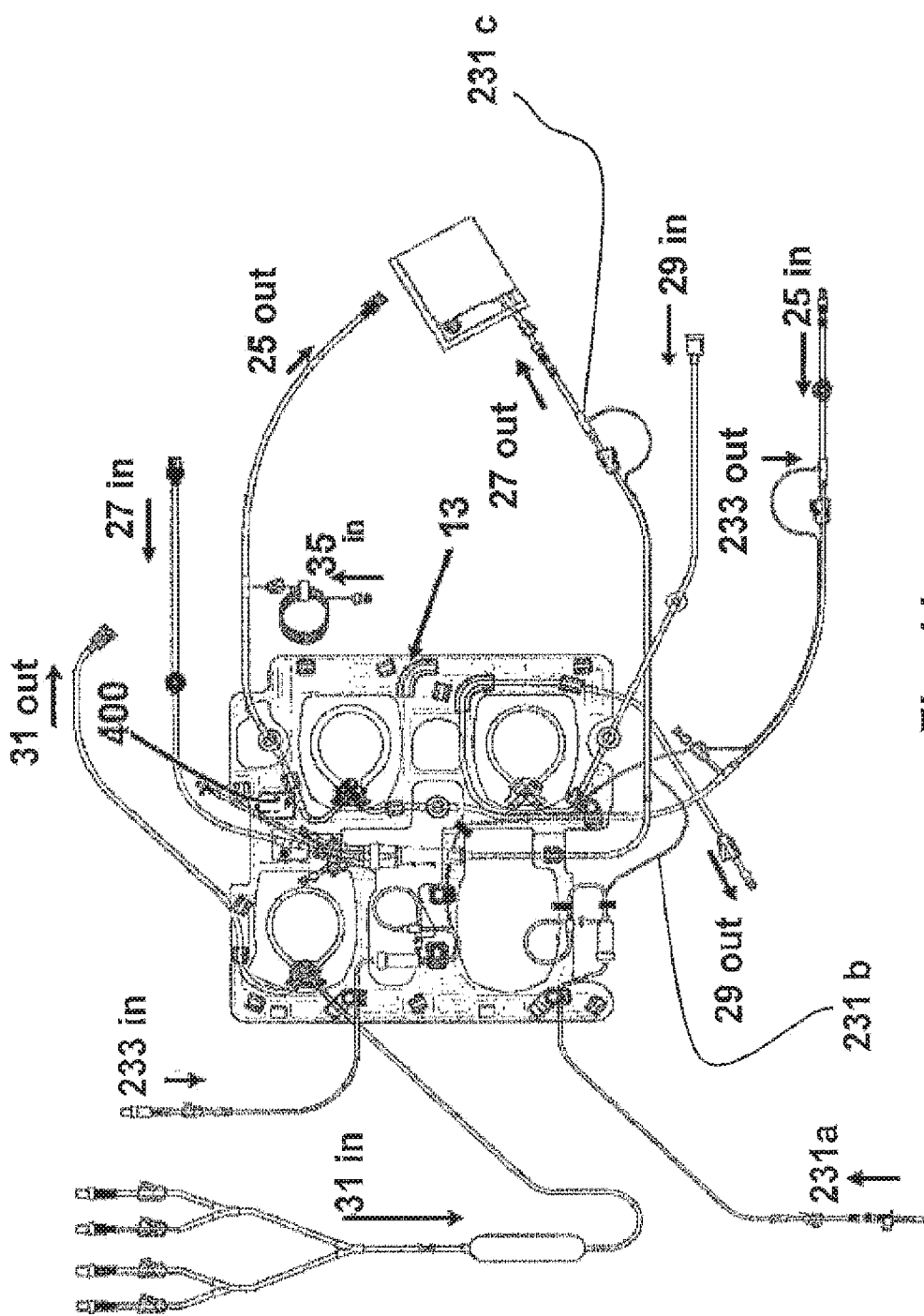
FIG. 11 schematically shows a tubing set comprising calcium and citrate addition sites.

FIG. 11 schematically shows a tubing set for a treatment comprising citrate-calcium addition.

The citrate-calcium tubing set arranged on an organizer 13 and identified by means of a specification feature 400, e.g. a yellow color label, comprises a calcium line 231a for adding calcium merging into a further segment 231b and opening into the venous return line 27out in a calcium addition site 231c for the addition of calcium.

Moreover, the citrate-calcium tubing set comprises a connector 233in for the citrate-calcium addition. Citrate solution is introduced via the respective line into the supply line 25in coming from the patient (i.e. into the arterial blood line) at the site, e.g. designated as 233out.

The citrate-calcium tubing set furthermore comprises a heparin addition site 35.

Figure 12:
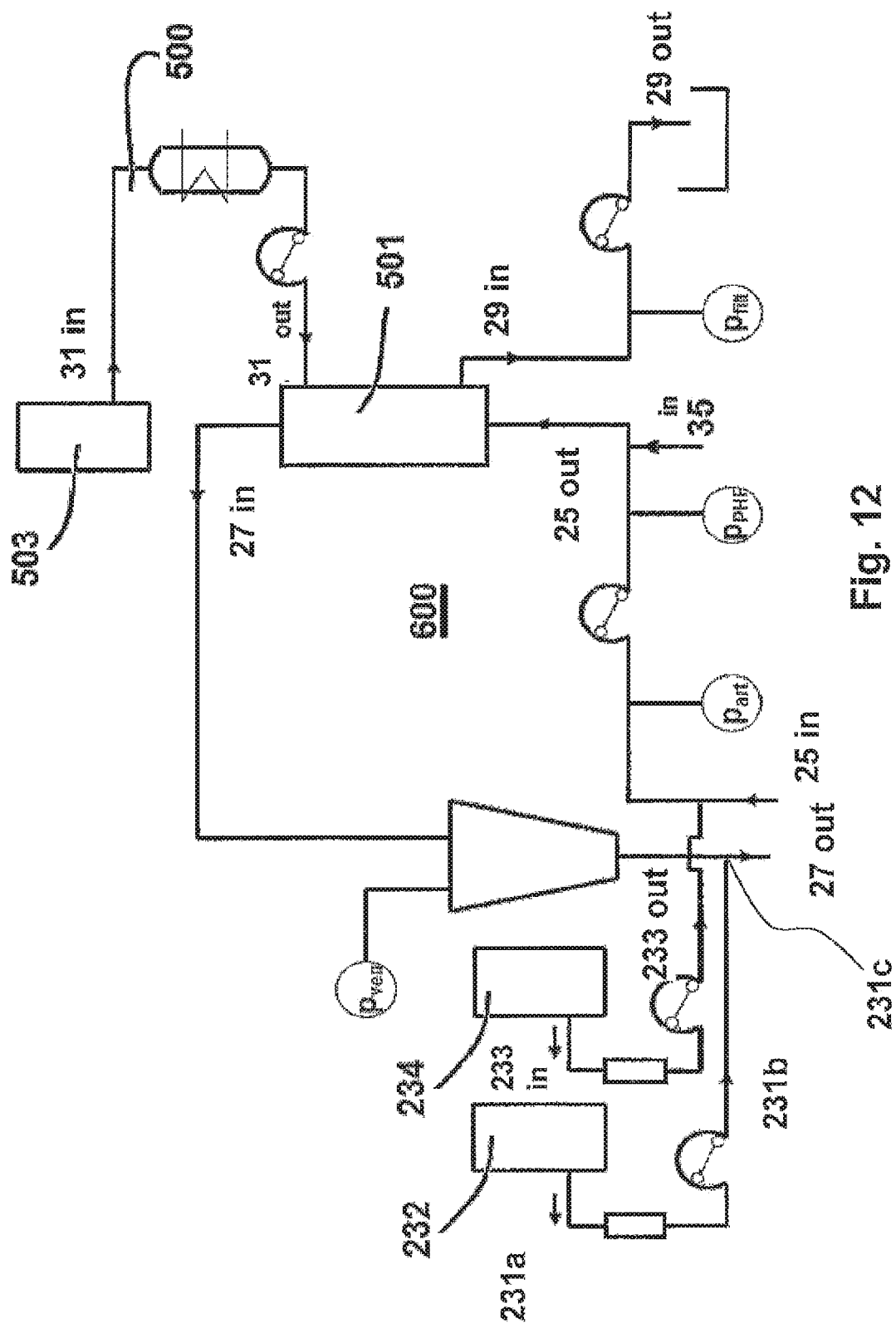
FIG. 12 schematically shows a diagram of an arrangement for performing a blood treatment comprising the addition of calcium and citrate.

FIG. 12 schematically shows a flow chart of an arrangement for performing a blood treatment comprising the addition of citrate as well as calcium by using a citrate-calcium tubing set as specified in FIG. 11.

FIG. 12 shows lines of the extracorporeal blood, circuit. 600 and of the dialysate circuit 500. Calcium is supplied from a calcium source 232 and citrate is supplied from a citrate source 234.

Figure 13:
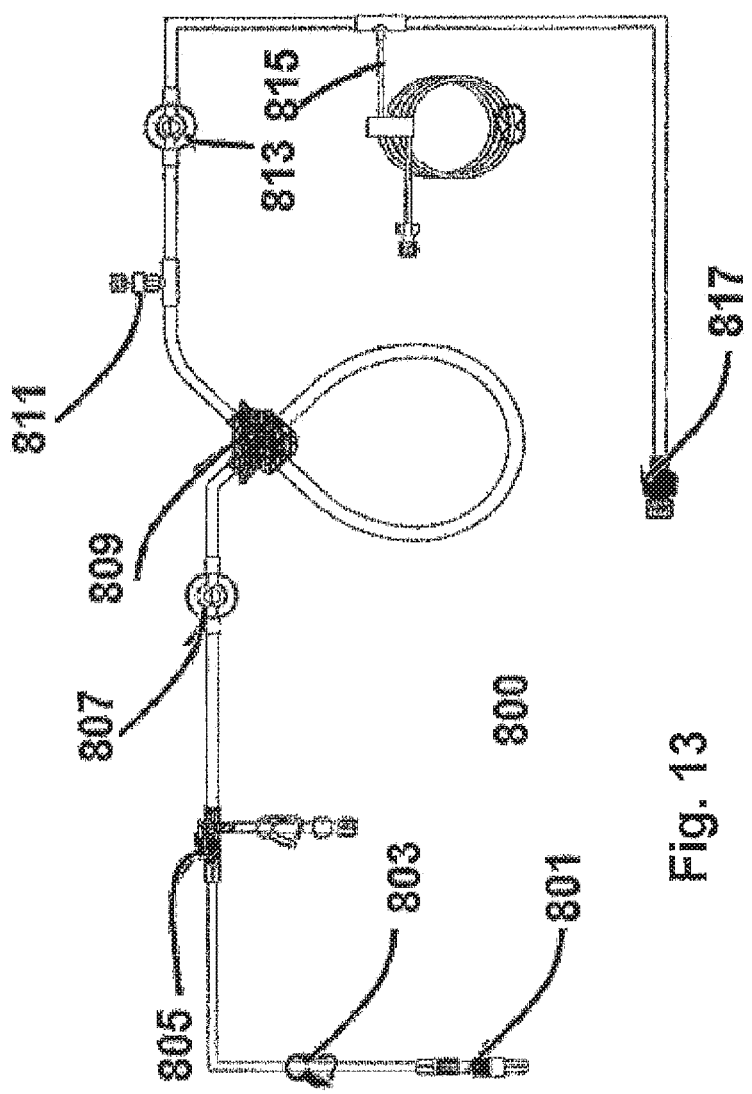
FIG. 13 schematically shows a supply line for a heparin treatment.

FIG. 13 schematically shows a supply line 800 substantially corresponding to the supply line 25 as, e.g. shown in FIG. 9, which is suited for a blood treatment using heparin addition.

The supply line 800 of FIG. 13 comprises a patient connector comprising a cap 801, a tubing clamp 803, an infusion port 805, a pressure measurement site 807 arranged in the supply line 800, a pump segment 809 for a roller pump, a connector 811 comprising a non-return valve for substitution liquid, a pressure measurement site 813 for a pre-filter pressure, a connector line 815 for a heparin syringe and a filter connector 817 comprising a cap.

Figure 14:
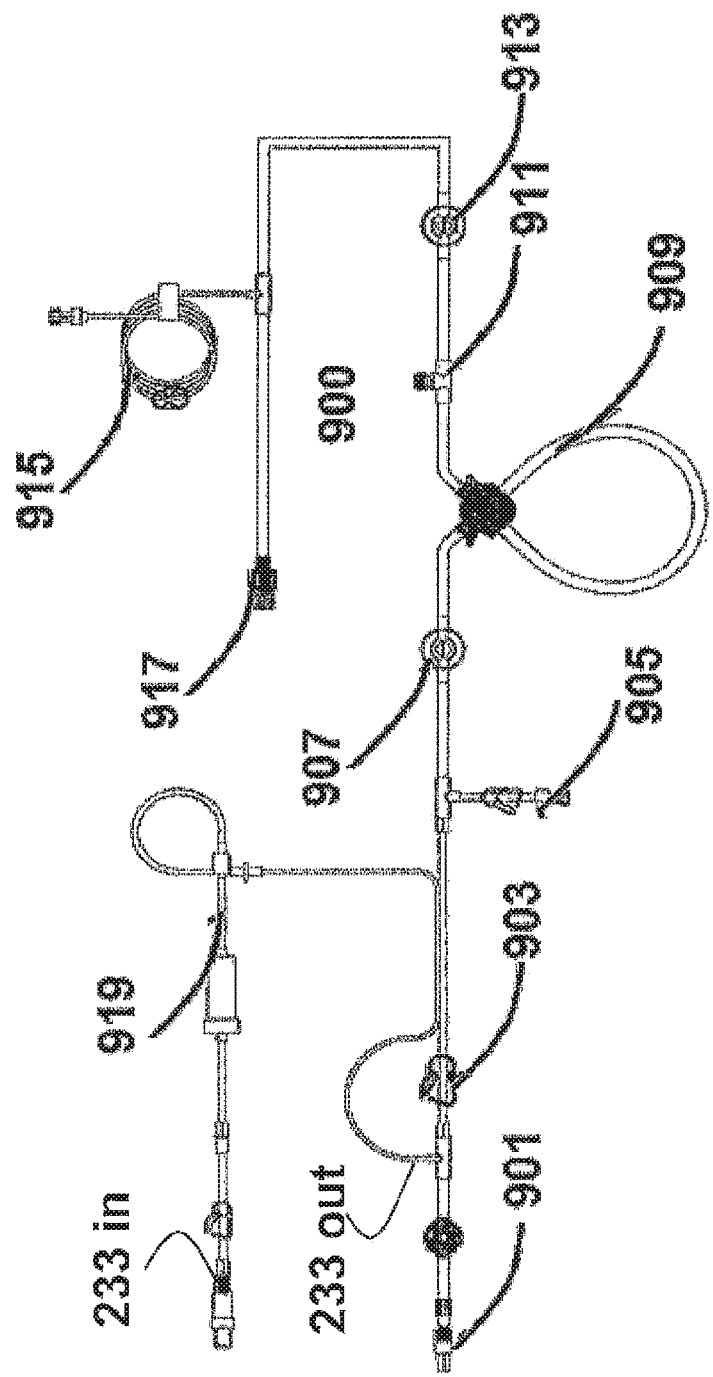
FIG. 14 schematically shows a supply line for a calcium and citrate treatment.

FIG. 14 schematically shows a supply line 900 substantially corresponding to the supply line 25 such as, e.g. shown in FIG. 11, which is suited for a blood treatment comprising the addition of both heparin and citrate.

As shown in FIG. 14, the supply line 900 comprising the citrate supply line 233in and 233out comprises a patient connector 901 comprising a cap, a tubing clamp 903, an infusion port 905, a pressure measurement site 907 arranged in the supply line 900, a pump segment 909 for a roller pump, a connector 911 comprising a non-return valve for substitution liquid, a pressure measurement site 913 for a pre-filter pressure, a connector line 915 for a heparin syringe, a filter connector 917 comprising a cap and a citrate supply line 919 comprising a pump segment and a drip chamber.

FIG. 15 schematically shows a return line 1100 substantially corresponding to the return line 27 as, e.g. shown in FIG. 11, which is suited for a blood treatment comprising calcium addition.

As shown in FIG. 15, the return line 1100 comprises a patient connector 1101 comprising a bag, a tubing clamp 1103, a calcium supply line 1105 comprising a pump segment, and a drip chamber, a venous bubble trap 1107, a pressure measurement line 1109 for the return pressure, a connector 1111 comprising a non-return valve for substitution liquid, a sampling site 1113 and/or an injection site as well as a filter connector 1115 comprising a cap.

FIG. 16A schematically shows a first cassette type comprising drip chambers 2315 and 2335 for calcium and citrate solutions as well as lines 231 and 233 for the addition of calcium and citrate and is thus designed or embodied as a citrate-calcium tubing set. The cassette of FIG. 16A is also suited or apt for heparin addition.

FIG. 16B schematically shows a second cassette type that does not comprise any components for citrate or calcium addition.

The cassette or functional means 300 of FIG. 16B is solely suited for heparin addition.

The specification features 400 of the two functional means therefore differ (e.g. yellow, if a citrate-calcium tubing set is present, see FIG. 16A, and blue, if no citrate-calcium tubing set is present, see FIG. 16B), what is herein indicated by means of the different shading of the specification features.

Figure 17:
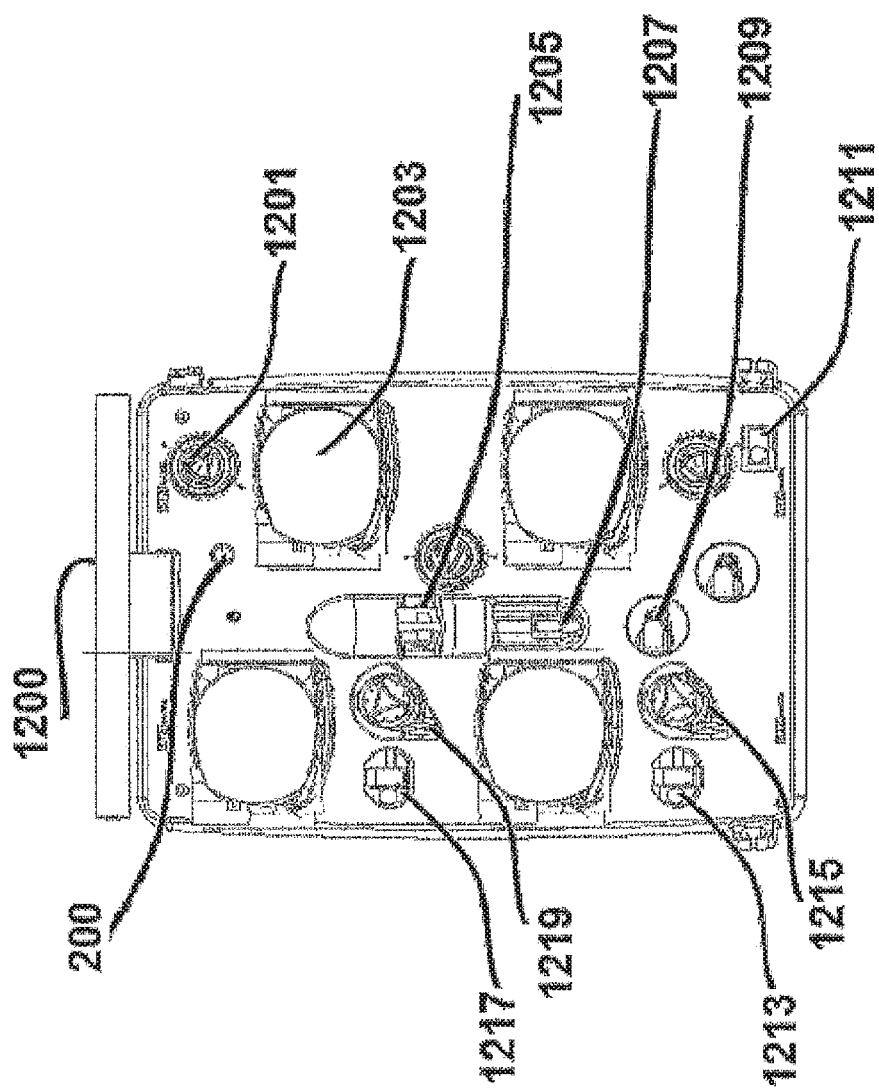
FIG. 17 schematically shows a machine front of a treatment apparatus according to the invention.

FIG. 17 schematically shows a machine front 1200 of a treatment apparatus according to the invention.

The machine front 1200 comprises a detection device 200 for detecting the specification feature of a functional means (both not shown in FIG. 17).

As shown in FIG. 17, the machine front 1200 of the treatment apparatus comprises a pressure measurement unit 1201, a pump 1203, a holder 1205 for a venous bubble trap, an air bubble detector 1207, e.g. in form of an optical detector, a tubing clamp 1209, a blood leakage sensor 1211, a holder 1213 comprising a control for a calcium drip chamber as well as a calcium pump 1215 comprising an insertion switch, a holder 1217 comprising a control for a citrate drip chamber as well as a citrate pump 1219 comprising an insertion switch.

Figure 18:
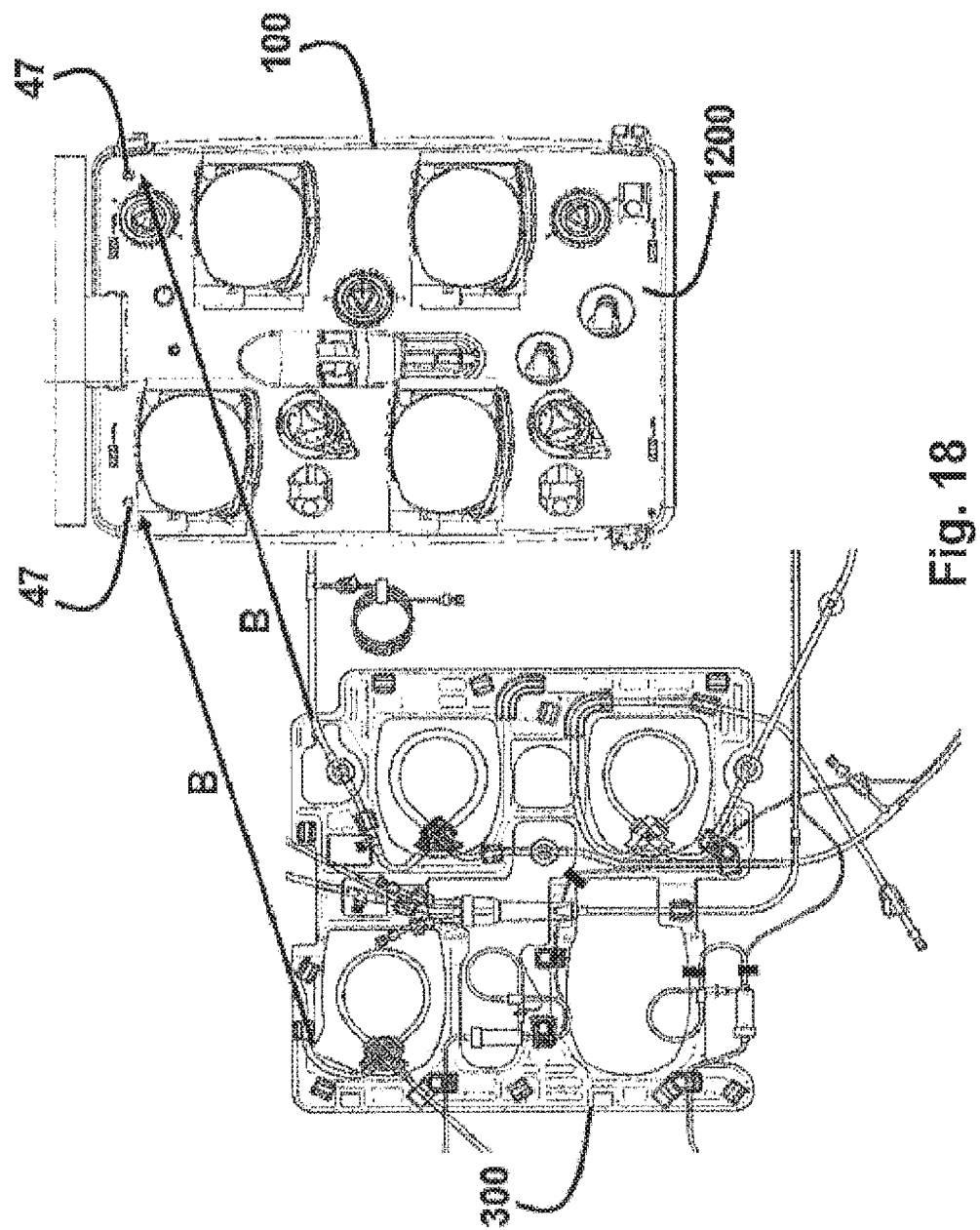
FIG. 18 schematically shows a possibility of positioning a functional means at the treatment apparatus.

FIG. 18 schematically shows a possibility of positioning a functional means 300 at the treatment apparatus 100.

For attaching or fixing the functional means 300 at the treatment apparatus 100, mounting pins 47 are provided at the treatment apparatus' 100 machine front 1200.

The two block arrows B indicate the direction of attaching or fixing the functional means 300 at the treatment apparatus 100.

In order to prepare or assemble the treatment apparatus 100 with the functional means 300, the tubing system of the functional means 300 is inserted into the corresponding segments of the treatment apparatus 100 and/or is connected therewith.

When assembling an acute dialysis machine with a cassette, for example, different elements of the blood tubing set are "inserted" into respective reception elements (e.g. clamps, roller pumps, etc.) at the machine front 1200 by the user. According to the treatment option that has been pre-selected by means of the machine control, according to the invention, machine control (control unit)—and optionally a corresponding sensor system at the dialysis machine—stepwise controls if all components are inserted properly as regards the pre-selected treatment option. Thereby, a set of automatic safety queries is related or associated with the pre-selected treatment option and the related detected cassette comprising its specific elements.

Figure 19:
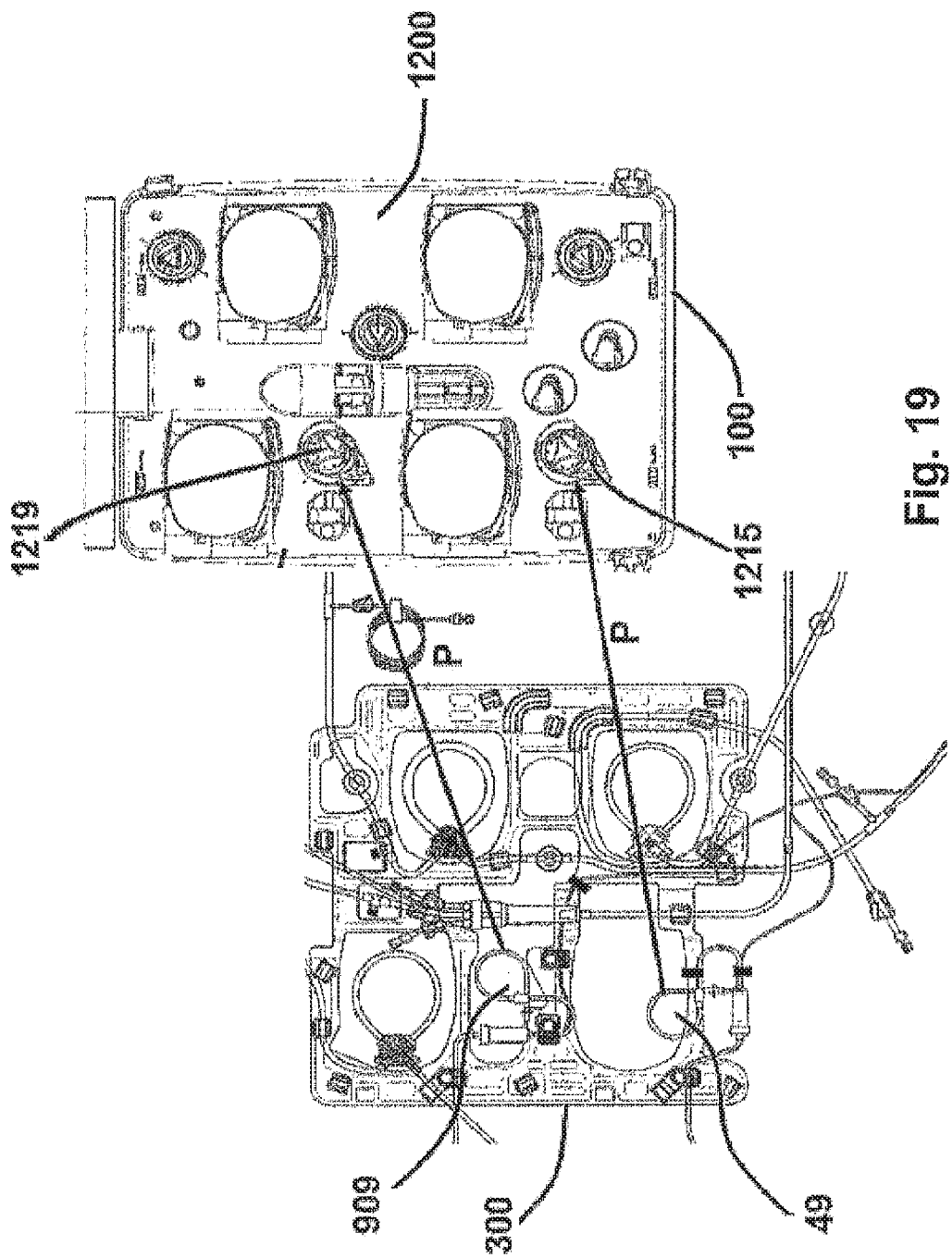
FIG. 19 schematically shows the insertion of pump segments of a functional means at the treatment apparatus.

FIG. 19 schematically shows the insertion of pump segments, pump segment 909 for citrate supply and pump segment 49 for calcium supply, of a functional means 300 at the treatment apparatus 100.

FIG. 20 schematically shows the insertion of drip chambers of a functional means 300 comprising a citrate-calcium addition at the treatment apparatus 100.

A citrate drip chamber 51 of the functional means 300 is inserted into the holder 1217 for the citrate drip chamber of the treatment apparatus 100; a calcium drip chamber 53 of the functional means 300 is inserted into the holder 1213 for the calcium drip chamber at the treatment apparatus 100. The two block arrows B in turn indicate the direction of attaching or fixing the functional means 300 at the treatment apparatus 100.

FIG. 21 schematically shows a detection of the functional means 300 or of its specification feature 400 by means of the treatment apparatus 100 according to the invention or of the detection device 200 thereof.

The block arrow P illustrates the positioning of the functional means 300 or of the specification feature 400 before or relative to the treatment apparatus 100 or the detection device 200 thereof.

For example, when arranging the functional means 300 at the coupling surface of the treatment apparatus manually, the blood treatment apparatus automatically identifies by means of the detection device 200, e.g. a color identification sensor (RGB sensor), if a yellow or a blue color label (specification feature 400; "yellow", e.g. for the addition of citrate-calcium; "blue", e.g. for the addition of heparin) is present. Depending on the earlier selection of the treatment option at the treatment apparatus 100, the control unit differentiates between different proper cases and possible fault or error situations (see above).

As, according to the invention, advantageously different tubing systems can be differentiated specifically for different types of anticoagulation of the extracorporeal blood circuit by means of a machine-readable label, it may advantageously be possible to avoid the risk of loss of blood and/or infusion of air resulting from open tubing ends and tubing system components not being inserted by means of the specific safety queries adopted to specific components of the identified tubing system.

The invention claimed is:

1. A disposable fluid line assembly coupleable with a blood treatment apparatus, the fluid line assembly comprising:
   a blood line;
   a solution supply line connected to the blood line to supply a solution to the blood line;
   an organizing structure configured to hold the blood line and the solution supply line; and
   an identification element, coupled to the disposable fluid line assembly and readable by the blood treatment apparatus, to indicate functional information about the fluid line assembly or to indicate at least one suitability of the disposable fluid line assembly for an application or use of the disposable fluid line assembly in the course or in association with at least one of: (i) a medical treatment effected by the blood treatment apparatus and (ii) a selected medical treatment option,
   wherein the solution supply line is a first solution supply line and the fluid line assembly further comprises a second solution supply line,
   wherein the blood treatment apparatus uses the functional information indicated by the identification element to identify particular types of solutions to be individually supplied to the blood line by each of the first solution supply line and the second solution supply line, and
   wherein the particular types of solutions to be individually supplied to the blood line by each of the first solution supply line and the second solution supply line are citrate and calcium respectively.

2. The fluid line assembly of claim 1, wherein the identification element is selected from the group consisting of: a barcode, a dot matrix code, a RFID chip, and a color label.

3. The fluid line assembly of claim 1, wherein the organizing structure has a coupling surface configured to be functionally coupled to the blood treatment apparatus.

4. The fluid line assembly of claim 3, and wherein the identification element is positioned on the coupling surface.

5. The fluid line assembly of claim 1, wherein the identification element is located on a side of the organizing structure which is, in use, positioned in front of the blood treatment apparatus.

6. The fluid line assembly of claim 1, further comprising a drip chamber coupled in in at least one of each of the first solution supply line and the second solution supply line.

7. The fluid line assembly of claim 1, wherein the fluid line assembly is embodied as a cassette.

8. The fluid line assembly of claim 1, wherein the identification element indicates a specific embodiment of the blood line.

9. The fluid line assembly of claim 1, wherein the identification element is a yellow color mark or label.

10. The fluid line assembly of claim 1, comprising a third solution supply line, wherein the solution to be individually supplied to the blood line by the third solution supply line is heparin.

11. An extracorporeal blood treatment system comprising:
    a blood treatment apparatus comprising a control unit and a detection device in communication with the control unit; and
    a fluid line assembly coupleable with the blood treatment apparatus to perform an extracorporeal blood treatment, the fluid line assembly comprising:
    a blood line;
    a solution supply line connected to the blood line to supply solution to the blood line;
    an organizing structure configured to secure the blood line and the solution supply line thereto; and
    an identification element, coupled to the disposable fluid line assembly and readable by the detection device, to indicate functional information about the fluid line assembly to the blood treatment apparatus or to indicate at least one suitability of the disposable fluid line assembly for an application or use of the disposable fluid line assembly in the course or in association with at least one of: (i) a medical treatment effected by the blood treatment apparatus and (ii) a selected medical treatment option,
    wherein the solution supply line is a first solution supply line and the fluid line assembly further comprises a second solution supply line,
    wherein the blood treatment apparatus uses the functional information indicated by the identification element to identify particular types of solutions to be individually supplied to the blood line by each of the first solution supply line and the second solution supply line, and
    wherein the particular types of solutions to be individually supplied to the blood line by each of the first solution supply line and the second solution supply line are citrate and calcium respectively.

12. The extracorporeal blood treatment system of claim 11, wherein the control unit is configured to compare a treatment option selected by a user at the blood treatment apparatus with the functional information or the suitability of the disposable fluid line assembly for an application or use indicated by the identification element.

13. The extracorporeal blood treatment system of claim 12, wherein the control unit is configured to cause an alarm or alert in response to determining an incompatibility between the treatment option and the functional information indicated by the identification element.

14. The extracorporeal blood treatment system of claim 11, wherein the control unit is configured to determine, based on the functional information or the suitability of the disposable fluid line assembly for an application or use indicated by the identification element, if the fluid line assembly is compatible with the selected treatment or treatment option and should be functionally coupled to the blood treatment apparatus.

15. The extracorporeal blood treatment system of claim 14, wherein the control unit is configured to cause an alarm or alert in response to determining if the fluid line assembly is not compatible with the selected treatment or treatment option selected at the blood treatment apparatus.

16. The extracorporeal blood treatment system of claim 11, wherein the extracorporeal blood treatment apparatus is either an apparatus for (i) apheresis, (ii) dialysis, (iii) for hemodialysis, (iv) for hemofiltration, or (v) for hemodiafiltration.

17. The extracorporeal blood treatment system of claim 11, wherein, during the extracorporeal blood treatment and based on the functional information indicated by the identification element, the control unit is configured to control an addition of an anticoagulant solution to the blood line.

18. The extracorporeal blood treatment system of claim 11, wherein the blood treatment apparatus comprises a roller pump for conveying solution through the solution supply line.

19. The extracorporeal blood treatment system of claim 11, further comprising a respective drip chamber coupled in each of the first solution supply line and the second solution supply line.

20. The extracorporeal blood treatment system of claim 11, further comprising a third solution supply line.

21. The extracorporeal blood treatment system of claim 20, wherein the particular types of solutions to be individually supplied to the blood line by each of the first solution supply line, the second solution supply line, and the third solution supply line are citrate, calcium, and heparin respectively.

22. An extracorporeal blood treatment system comprising:
a blood treatment apparatus comprising a control unit and a detection device in communication with the control unit; and
a fluid line assembly coupleable with the blood treatment apparatus to perform an extracorporeal blood treatment, the fluid line assembly comprising:
a blood line;
a solution supply line connected to the blood line to supply solution to the blood line;
an organizing structure configured to secure the blood line and the solution supply line thereto; and
an identification element, coupled to the disposable fluid line assembly and readable by the detection device, to indicate functional information about the fluid line assembly to the blood treatment apparatus or to indicate at least one suitability of the disposable fluid line assembly for an application or use of the disposable fluid line assembly in the course or in association with at least one of: (i) a medical treatment effected by the blood treatment apparatus and (ii) a selected medical treatment option,
wherein the solution supply line is a first solution supply line and the fluid line assembly further comprises a second solution supply line and a third solution supply line,
wherein the blood treatment apparatus uses the functional information indicated by the identification element to identify particular types of solutions to be individually supplied to the blood line by each of the first solution supply line, the second solution supply line, and the third solution supply line, and
wherein the particular types of solutions to be individually supplied to the blood line by each of the first solution supply line, the second solution supply line, and the third solution supply line are citrate, calcium, and heparin respectively.

* * * * *

UNITED STATES PATENT AND TRADEMARK OFFICE
CERTIFICATE OF CORRECTION

PATENT NO. : 10,420,875 B2
APPLICATION NO. : 15/407571
DATED : September 24, 2019
INVENTOR(S) : Josef Beden and Juergen Klewinghaus It is certified that error appears in the above-identified patent and that said Letters Patent is hereby corrected as shown below:

In the Claims

Column 23, Line 45, in Claim 6, delete "in in" and insert --in--.

Signed and Sealed this
Fifth Day of May, 2020

Andrei Iancu
*Director of the United States Patent and Trademark Office*